(12) United States Patent
Kim et al.

(10) Patent No.: US 6,841,180 B2
(45) Date of Patent: Jan. 11, 2005

(54) METHOD FOR PREPARING LACTIC ACID FERMENTED SOLUTION OF MUSHROOM AND LACTIC ACID FERMENTED SOLUTION OF MUSHROOM PRODUCED THEREBY

(75) Inventors: Beom Kyu Kim, Sacheon-shi (KR); Gab-Gyun Shin, Chinju-shi (KR); Jae Young Cha, Pusan-shi (KR); Beong Sam Jeon, Masan-shi (KR); Dong Won Bae, Chinju-shi (KR)

(73) Assignee: Biohub Co., Ltd., Chinju-shi (KR)

( * ) Notice: Subject to any disclaimer, the term of this patent is extended or adjusted under 35 U.S.C. 154(b) by 398 days.

(21) Appl. No.: 10/001,970

(22) Filed: Dec. 5, 2001

(65) Prior Publication Data

US 2002/0192334 A1 Dec. 19, 2002

(30) Foreign Application Priority Data

| May 7, 2001 | (KR) | ................................. | 2001-24513 |
| Sep. 4, 2001 | (KR) | ................................. | 2001-54236 |
| Nov. 22, 2001 | (KR) | ................................. | 2001-73033 |

(51) Int. Cl.[7] .............................................. A23L 1/28
(52) U.S. Cl. ........................................... 426/7; 426/60
(58) Field of Search ........................ 426/7, 49, 34, 426/60

(56) References Cited

U.S. PATENT DOCUMENTS 4,324,806 A * 4/1982 Schmitz ....................... 426/52

5,028,441 A * 7/1991 Ikeda ........................... 426/49

FOREIGN PATENT DOCUMENTS

| JP | 51-057858 | * | 5/1976 |
| JP | 36-2122554 | * | 6/1987 |
| JP | 63-68069 | * | 3/1988 |
| JP | 4-30745 | * | 2/1992 |
| JP | 10118680 | * | 5/1998 |
| JP | 11046684 | * | 2/1999 |
| KR | 165939 | | 3/1998 |
| KR | 195886 | | 8/1998 |

OTHER PUBLICATIONS

Tamime et al. Yoghurt Science and Technology. Pergamom Press. First edition, 1985. p. 276–281.*

* cited by examiner

Primary Examiner—Keith Hendricks
(74) Attorney, Agent, or Firm—Greenblum & Bernstein, P.L.C.

(57) ABSTRACT

Lactic acid fermented solution of mushroom produced in accordance with the method for preparing lactic acid fermented solution of mushroom comprising the steps of (a) preparing a mushrooms ingredients-containing medium; (b) inoculating lactic acid strain onto the medium; (c) culturing the strain-inoculated medium; and (d) aging the cultured medium is excellent in its taste, flavor and gustatoriness, and exhibits an inhibitory effect against the formation of peroxidized lipid and a dropping effect against blood sugar level.

17 Claims, 14 Drawing Sheets

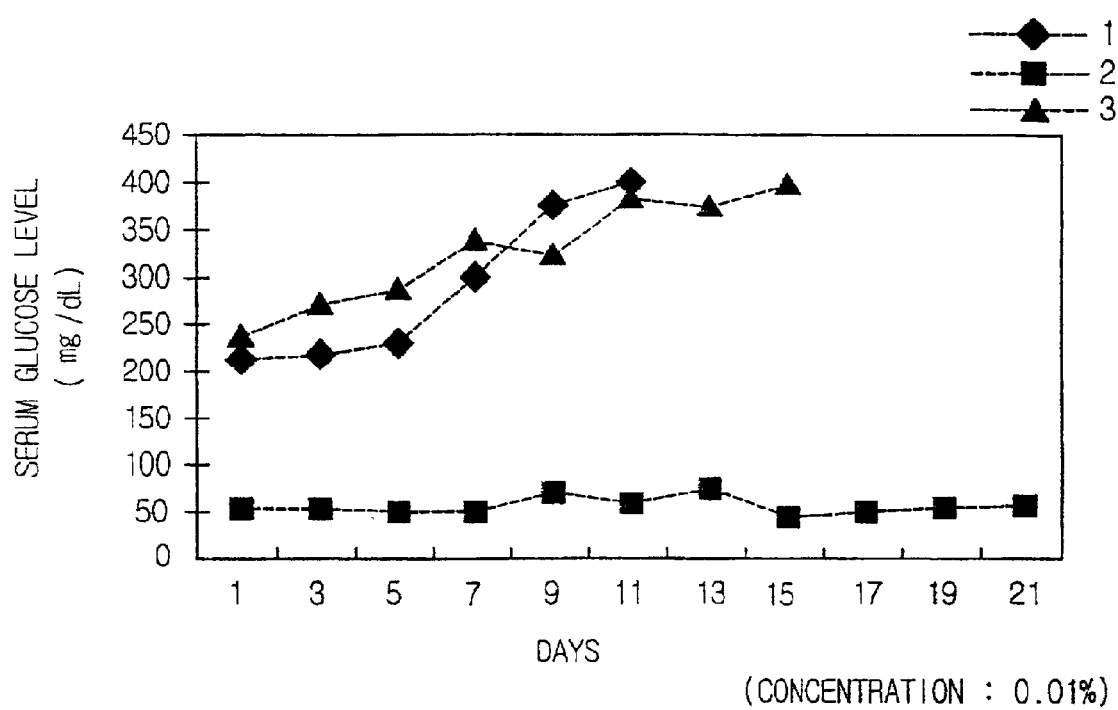

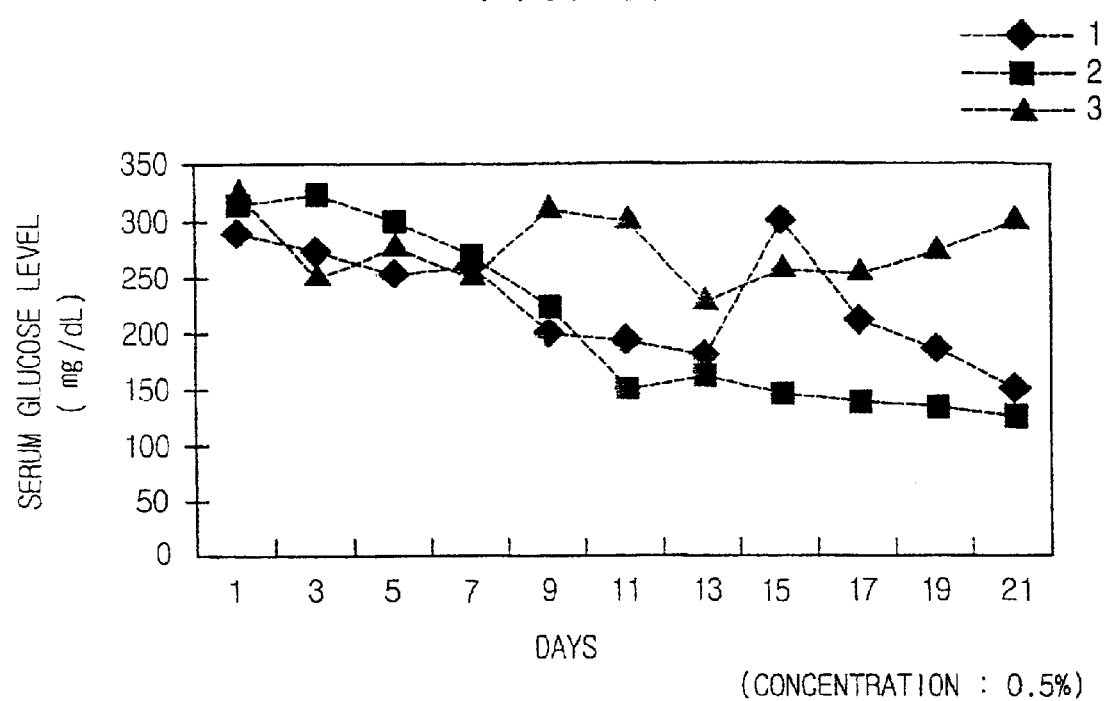

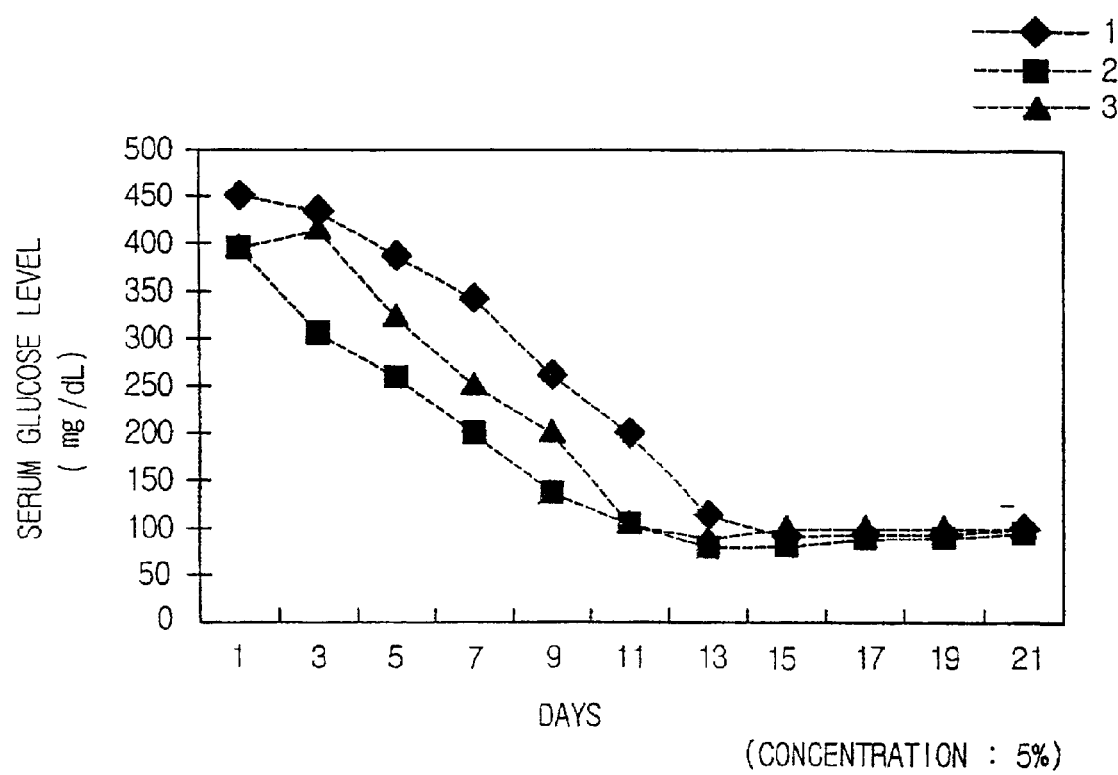

A: FEEDING OF LACTIC ACID FERMENTED SOLUTION CONTANINING 2% OF MUSHROOM EXTRACT (EXAMPLE 42, 0~36 DAYS)
B: FEEDING CUT (37~42 DAYS)
C: FEEDING OF MUSHROOM EXTRACT (43~60 DAYS)

METHOD FOR PREPARING LACTIC ACID FERMENTED SOLUTION OF MUSHROOM AND LACTIC ACID FERMENTED SOLUTION OF MUSHROOM PRODUCED THEREBY

TECHNICAL FIELD

The present invention relates to a method for preparing lactic acid fermented solution of mushroom and a lactic acid fermented solution of mushroom produced thereby, and more particularly, to a method for preparing lactic acid fermented solution of mushroom which comprises the steps of inoculating a lactic acid strain onto a mushroom ingredients-containing medium and fermenting said medium under appropriate conditions and a lactic acid fermented solution of mushroom produced thereby. The lactic acid fermented solution of mushroom thus obtained is excellent in its taste, flavor and gustatoriness, and is effective for inhibiting the formation of peroxidized lipid and the drop of blood sugar level.

BACKGROUND ART

Generally, a mushroom contains lower fat but higher protein and saccharide contents than any other plant. The saccharide also includes trehalose, mannitol, arabinose and the like together with polysaccharide that are hard to absorb into human intestinal tracts and of which main component is an indigestible dietary fiber. Therefore, mushroom is a food material having lower calories than those calculated by food analysis. Furthermore, ergosterol and calcium are commonly included in an amount of 100–800 mg per an individual, and they are conversed into vitamin $D_2$ when dried. In addition to said ingredients, mushroom contains vitamin $B_1$, vitamin $B_2$ and niacin, not vitamins A and C. Also, as minerals, K is included in a higher portion than Na therein, and P, Ca and Fe follow. Flavorous ingredients of mushroom are mainly nucleic acid and a combination of glutamic acid, succinic acid, malic acid, uric alcohol, etc. Therefore, mushroom is a food material not only having low calories and capable of exerting physiological functions, but also excellent in flavor, taste and gustatoriness.

However, mushroom includes so large amounts of water and nitrogen compounds that it decays and microorganism is easy to propagate due to its soft tissue. Accordingly, the shelf life after harvest of mushroom is short. Mushroom is distributed in the form of live or dried product. Because mushroom is used as a side dish or a flavoring, it plays a role in providing elementary nutrients.

Recently, mushroom has been known to an effective material for inhibiting against cancer and variability, for dropping the formation of lipid in serum, for enhancing immunity to diseases, for inhibiting aging, and for preventing adult diseases. So far, the use of mushroom has been expanded into medicinal field. As Such medicinal mushrooms, *Ganderma lucidum, Lentinus edodes, Pleurotus osteratus, Elfvingia applanata, agaricus, Auricularia auricula* and *Umbilicaria esculenta* have been expected. In particular, it is reported that polysaccharide protein complex included in *Ganderma lucidum* extract exhibits the inhibition of the proliferation of cancer cell, treatment of essential hypertension, inhibition of the formation of peroxidized lipid, etc. Also, *Lentinus edodes* is well known to have anticancer property, dropping effect against cholesterol tonicity, diuresis, and treatment of hypertension, nephritis, asthma, gastric ulcer, etc. and its extract is reported to have effects for dropping lipid in serum and liver and for inhibiting the liver damage. Also, the polysaccharide extract from *Pleurotus osteratus* were reported to have a dropping effect of cholesterol in serum and an inhibiting effect against liver injuries caused by carbon tetrachloride. Furthermore, an extract obtained from fruit bodies and mycelia of *Pleurotus osteratus* was reported to have an antioxidative effect.

Lactic acid bacterium is a bacterium that produces lactic acid using a carbohydrate such as glucose and lactose, and has been used in fermented milk and cheese from 3,000 B.C. Because of the fact that the milk fermented by lactic acid bacteria inhibits the growth of deleterious bacteria in digestive organs and prevents human aging, lactic acid bacteria fermented milk has been sold as goods worldwide to date. Many beneficial effects of lactic acid bacteria to human health have steadily been studied.

Such effects of lactic acid bacteria include an intestinal regulation (that is, prevention against diarrhea and constipation), suppression against the proliferation of intestinal cancers and aging by inhibiting the growth of deleterious bacteria, promotion of the growth by the formation of vitamins, prevention of adult diseases by controlling cholesterol, reinforcement of immunity, etc.

As typical examples of lactic acid bacteria are included *Streptococcus, Pediococcus, Leuconostoc*, lactic acid *bacillus, vipidus*, etc. Lactic acid bacteria are found in the natural world, e.g., digestive tracts of human and animals and almost all of vegetables. Bulgaria bacteria, yogurt bacteria and thermophilus bacteria have been used in the production of yogurt. Yogurt bacteria, casei bacteria and acidophilus bacteria used in the production of beverages containing lactic acid bacteria. Casei bacteria and milk *Streptococcus* has been used in the production of cheese. Milk *Streptococcus* has been used in the production of fermented butter. Each specific lactic acid bacterium has been used in the manufacturing processes of different kinds of food.

Lactic acid bacteria inhabit in the intestinal epithelial cell and do their metabolisms. Lactic acid bacteria secrete lactic acid, (lower) fatty acids, bacteriocin, $H_2O_2$, etc, so as to inhibit the growth of deleterious bacteria and to drop the formation of cholesterol by HMG (Hydroxy Methyl Glutaric), Orotic Acid, Uric Acid, etc, which are formed by the fermentation of lactic acid bacteria. Particularly, *Lactobacillus acidophilous* directly decomposes cholesterol. Lactic acid bacteria activate the microphage detecting bacillus in immune system, thereby detecting the appearance of bacteria and virus, inhibiting the proliferation of cancer cell due to lymphocytic division, increasing the production of 1 g A, an antibody in blood, and promoting the production of γ-interferon. Such series of functions improve the immunity, increase nutritional values of food, inhibit the endogenous infection, inhibit the formation of intestinal carcinogens, and derive the death of deleterious bacteria.

Recent changes of diet lead to the high possibilities of diseases in cerebrovascular system, diseases in circulatory system such as heart diseases, hypertension, hyperlipidemia and arteriosclerosis, and malignant tumors. Such chronic regressive diseases are associated with the disorder of lipid metabolism in a living body. Recently, physiologically active materials to improve human health has vigorously been searched and studied, and as a result, natural ingredients effective against lipid and oxidization have been found and reported. Among them, to edible and medicinal mushrooms have been paid attention as antioxidative materials.

The formation of free radical due to oxidative stress in a living body can peroxidate the biomembrane lipid and the increased peroxidized lipid can do damage to tissues and organs, resulting in metabolism disorder. Therefore, physiologically active matters capable of inhibiting the oxidative damages due to the formation of free radical in a living body are expected to contribute in lowering the occurrence of diseases in circulatory system and chronic diseases such as cancer.

Further, recent improvement of diet and changes of life style lead to fatness due to intake of high-caloric food and shortage of moderate exercise. The advance of industry and complex relationship in society provided the causes of stress. And the development of medicine has prolonged the span of life. These factors are causes of various diseases, particularly diabetes that is a cause of chronic vascular diseases, and increases the rate of death.

Diabetes mellitus is a disease characterized by inadequate secretion of insulin in pancreas or disorder of insulin receptor in each tissue and by high level of blood sugar. Diabetes mellitus is classified into insulin dependent diabetes mellitus (Type 1 Diabetes mellitus) and non-insulin dependent diabetes mellitus (Type 2 diabetes mellitus). Insulin dependent diabetes mellitus is occurred when pancreas β-cell secreting insulin due to disorder in immune system is destroyed, and non-insulin dependent diabetes mellitus is occurred by disorders in insulin receptor such as muscular cell due to heredity and fatness.

Recent studies for searching various physiologically active materials such as tea tree leaves, coix and mulberry leaves having effects for dropping the blood sugar level have continuously been progressed. But, these studies have mainly been concentrated on the treatment of type 1 diabetes mellitus.

According to the statistical data, the number of patients with type 1 diabetes mellitus of the two types is on an increasing trend yearly and, in Korea, 95% of patients with the diabetes mellitus fall on type 2 diabetes mellitus. Agents for dropping blood sugar level are administered orally to patients with type 2 diabetes mellitus together with dietary treatment. To this end, acarbose and voglibose are administered to patients for dropping the blood sugar level after meals, but they are sold at high prices.

To overcome these disadvantages, studies for dropping the blood sugar level using commercially available and edible food or various naturally originating physiologically active materials have been progressed. Korean Pat. No. 165,939 discloses a composition for dropping blood sugar level containing Chinese matrimony extract and a method for preparing the same. Korean Pat. No. 195,886 discloses pharmaceutical composition for treating diabetes mellitus containing Crdyceps spp, bezoar. Chinese matrimony, kudzu root, etc, However, the formulations for treating diabetes mellitus disclosed in said patents are not suitable in their taste, flavor and gustatoriness, and their preparing processes are very complicated.

Therefore, needs for a food composition effective for treating type 2 diabetes mellitus and a formulation suitable in taste, flavor and gustatoriness have been existed in this field.

As described above, mushroom and lactic acid bacteria are used as materials for health food, but synergistic effects thereof are not known yet.

DISCLOSURE OF INVENTION

Thus, the present inventors extensively studied to investigate the pharmacological effects of mushroom and lactic acid fermented solution. As a result, we found that lactic acid fermented solution of mushroom exhibits a potent synergistic effect, and then completed the present invention.

Therefore, it is an object of the present invention to provide a method for preparing lactic acid fermented solution of mushroom excellent in its taste, flavor and gustatoriness and shortened in fermentation period, and a lactic acid fermented solution of mushroom produced thereby.

It is another object of the present invention to provide a method for preparing lactic acid fermented solution of mushroom capable of inhibiting the formation of peroxidized lipid, and a lactic acid fermented solution of mushroom produced thereby.

It is another object of the present invention to provide a method for preparing lactic acid fermented solution of mushroom effective for dropping the blood sugar level, and a lactic acid fermented solution of mushroom produced thereby.

BRIEF DESCRIPTION OF THE DRAWINGS

FIGS. 6a–6e are graphs showing the change of blood sugar level over the dietary history of lactic acid fermented solutions of Ganderma lucidum obtained in Comparative Example 1, Example 40, Example 41, Comparative Example 2 and Example 42, respectively.

BEST MODE FOR CARRYING OUT THE INVENTION

Figure 1:
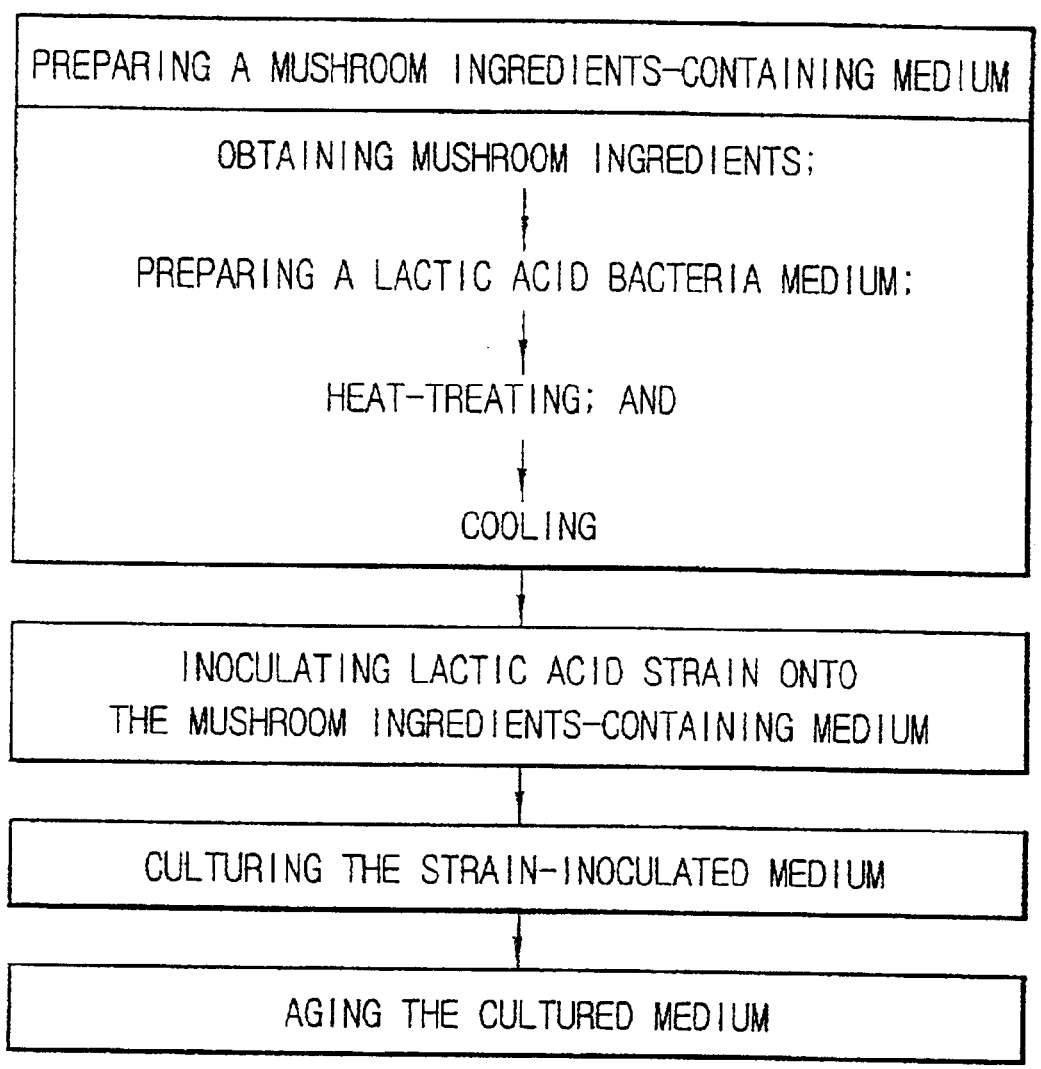
FIG. 1 is a schematic of the process for preparing lactic acid fermented solution of mushroom according to the present invention.
Figure 2:
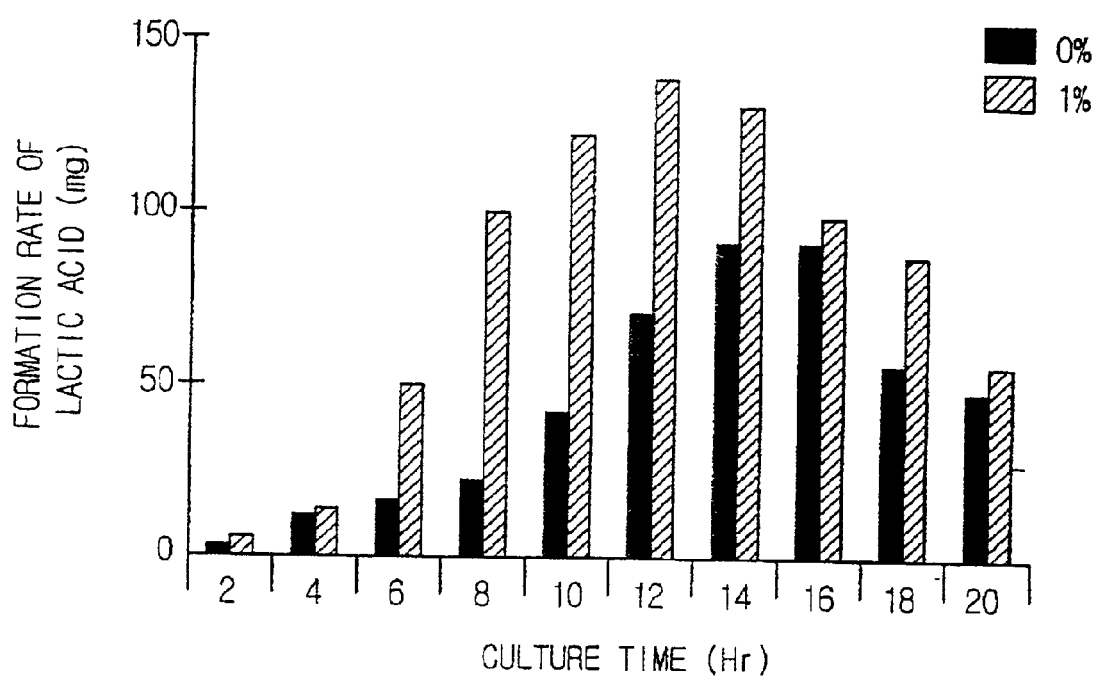
FIG. 2 is a graph showing the formation rate of the lactic acid fermented solution of Pleurotus osteratus obtained in Example 37 according to the present invention.
Figure 3:
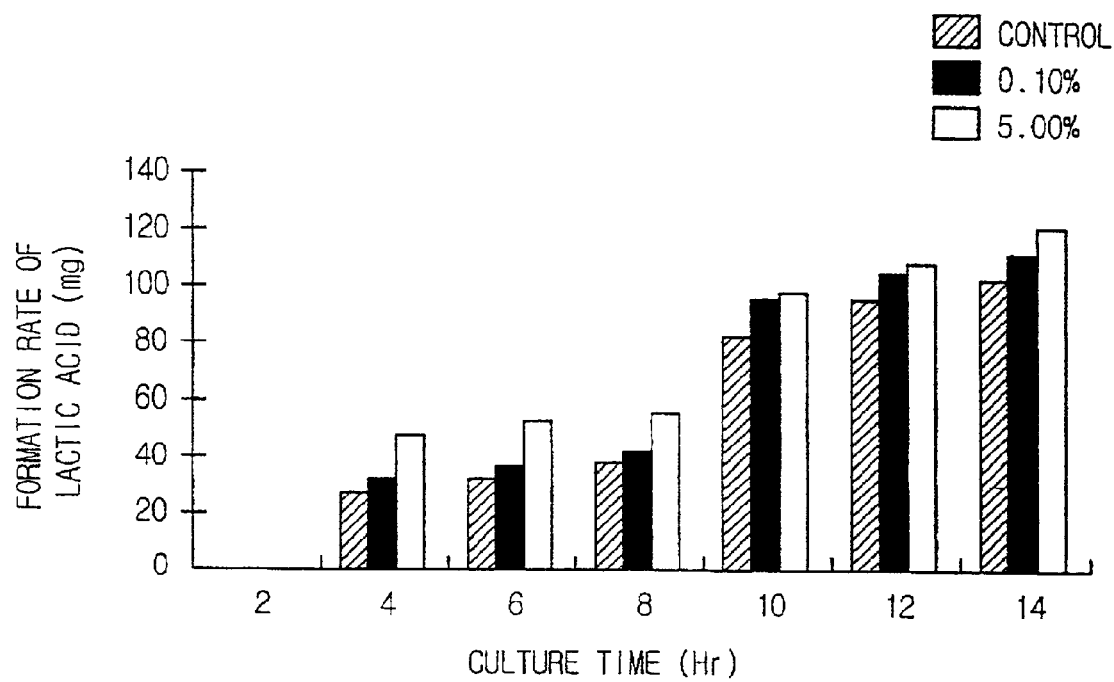
FIG. 3 is a graph showing the formation rate of lactic acid fermented solution of Ganderma lucidum obtained in Example 38 according to the present invention.
Figure 4A:
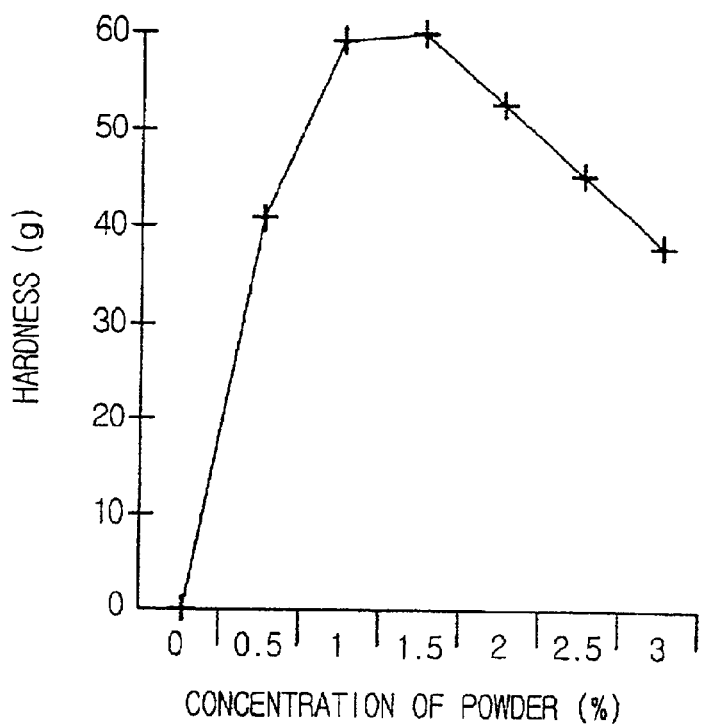
FIGS. 4a–4c are graphs showing rheologies of lactic acid fermented solution of Pleurotus osteratus obtained in Example 37 according to the present invention.
Figure 4B:
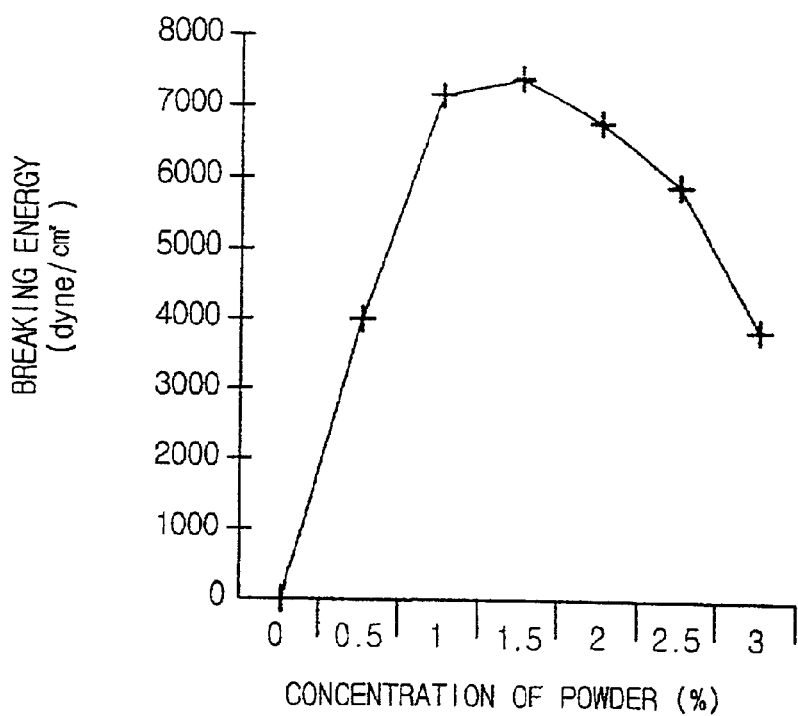
Figure 4C:
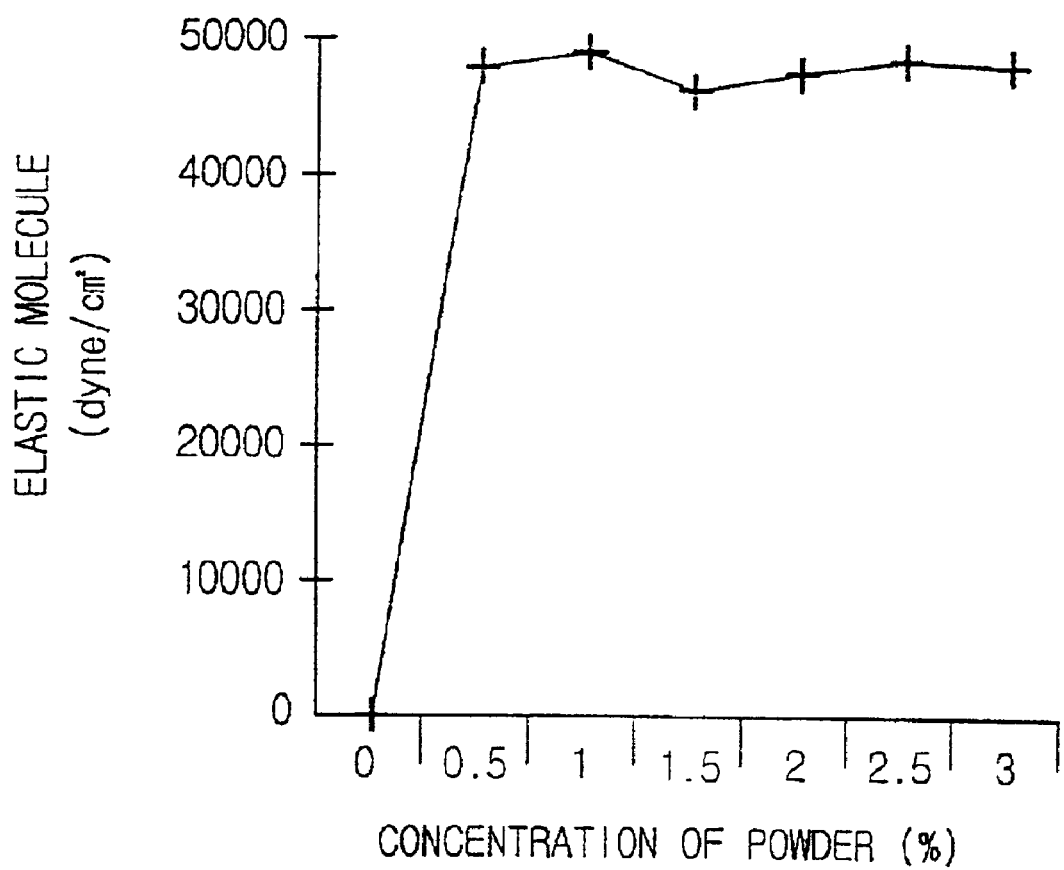
Figure 5A:
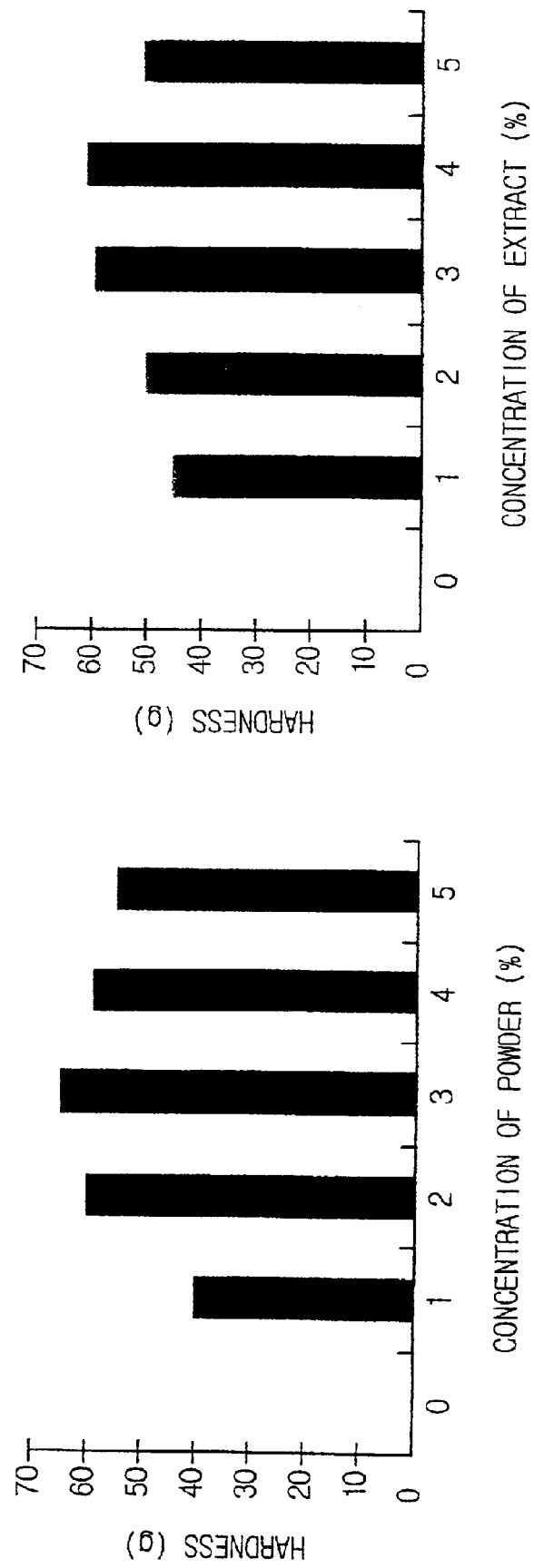
FIGS. 5a–5c are graphs showing rheologies of lactic acid fermented solution of Ganderma lucidum obtained in Example 38 according to the present invention.
Figure 5B:
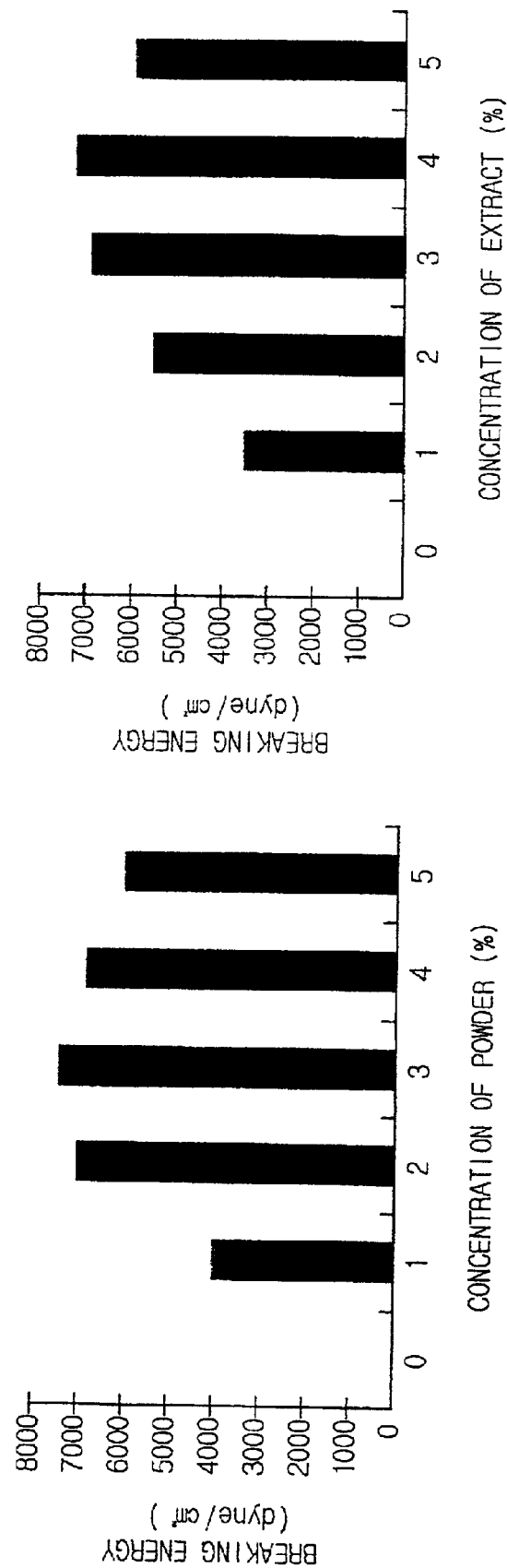
Figure 5C:
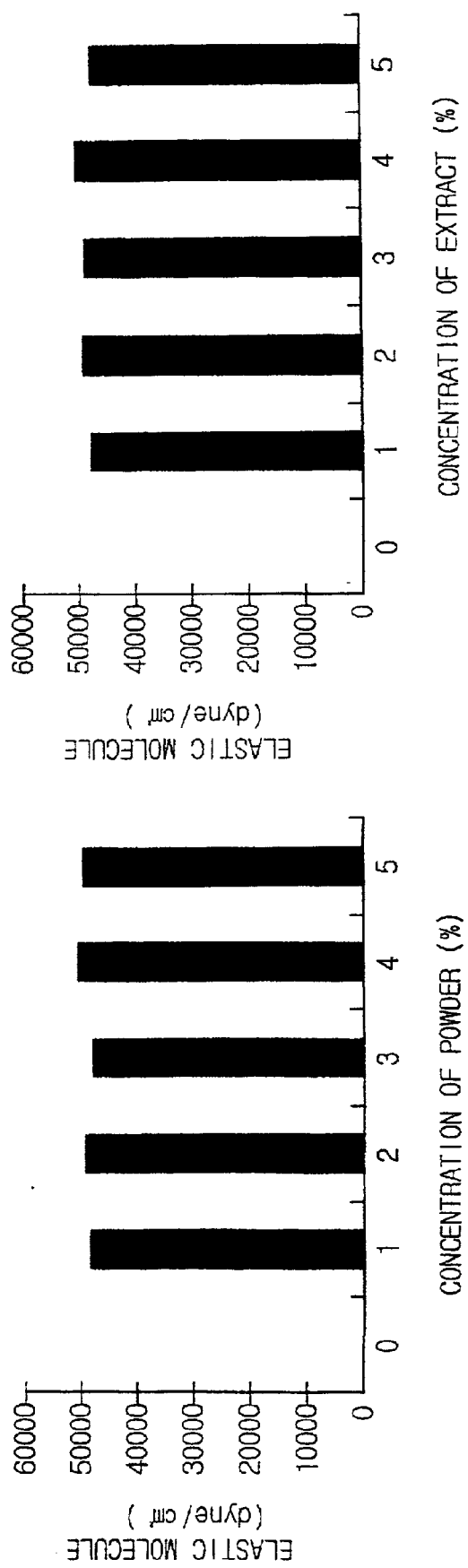
Figure 6B:
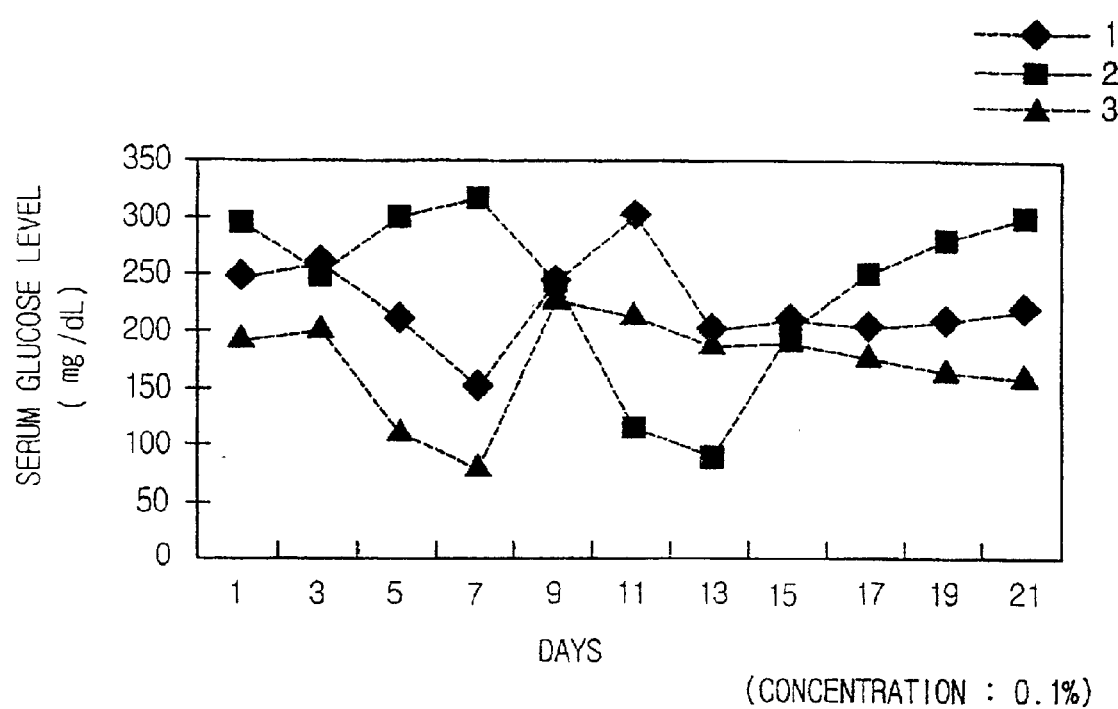
Figure 6D:
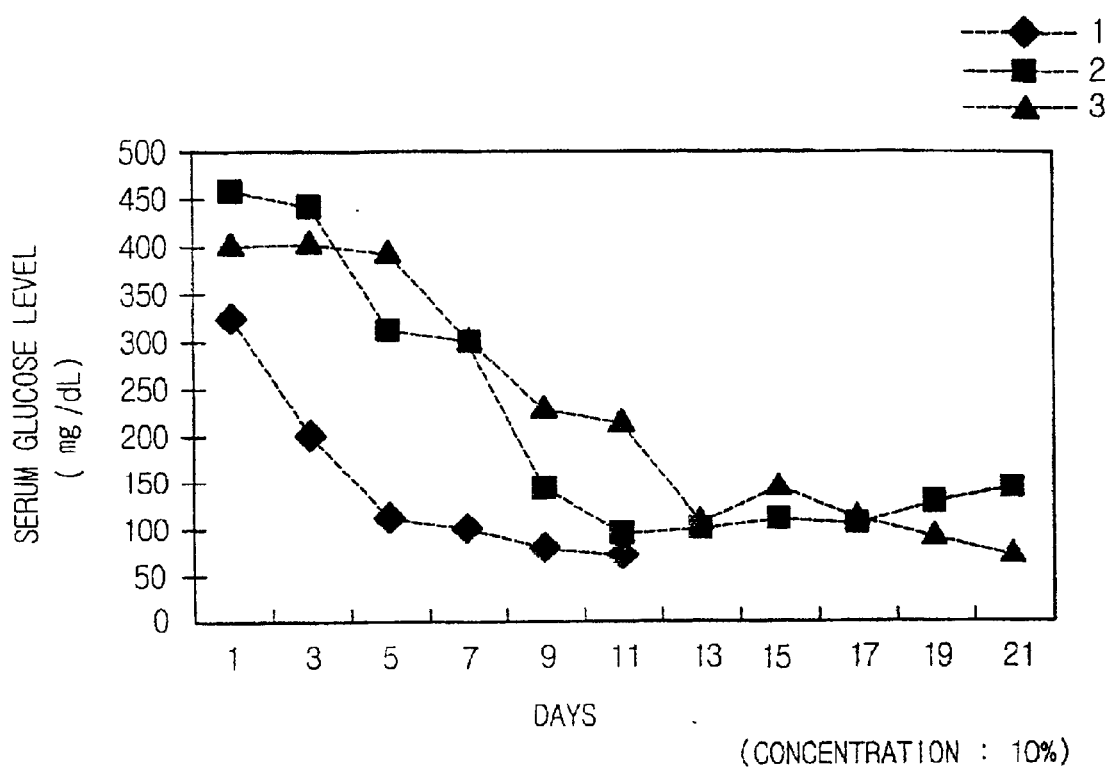

A method for preparing lactic acid fermented solution of mushroom according to the present invention comprises the steps of a) preparing a mushroom ingredients-containing medium;
b) inoculating lactic acid strain onto the medium;
c) culturing the strain-inoculated medium; and
d) aging the cultured medium.

Also, said step (a) comprises the steps of i) obtaining mushroom ingredients from fruit bodies or mycelia of mushroom by grinding or extracting; ii) adding 0.1–10% by weight of the obtained mushroom ingredients, 1–50% by weight. preferably 1–20% by weight of defatted milk, 0.1–20% by weight of sugar and the balance of purified water to the zip mushroom ingredients-containing medium and homogenizing the mixture to prepare a lactic acid bacteria medium; iii) heat-treating the ingredients-containing medium of mushroom at a temperature ranging 75–110° C. for 15–40 minutes; and iv) cooling the heat-treated medium to a temperature ranging 35–40° C.

Examples of mushrooms usable in said i) include all of edible and medicinal mushrooms, e.g. *Agaricus blazei, Ganderma lucidum, Grifola frondosa, Elfvingia applanata, Pleurotus osteratus, Agaricus bisporus, Flammulina velutipes, Lentinus edodes* and *Crdyceps* spp., but are not limited to them. The parts of the usable mushrooms are fruit bodies and mycelia. In case of *Agaricus blazei, Ganderma lucidum, Grifola frondosa* and *Elfvingia applanata,* the mushroom ingredients are obtained from their fruit bodies and mycelia are used. And in case of *Pleurotus osteratus, Agaricus bisporus, Flammulina velutipes, Lentinus edodes* and *Crdyceps* spp., the mushroom ingredients are obtained their fruit bodies. Also, mushroom ingredient is preferably a mixture of powder and extract from mushroom. In particularly, mushroom ingredient for dropping the blood sugar level is preferably an extract from *Ganderma lucidum.*

In step b), 1–10% by weight of lactic acid bacteria in cold storage or heat-treated lactic acid bacteria, based on the total weight of said mushroom ingredients-containing medium, is inoculated onto the-medium cooled in iv) of the step a). At this time, the inoculated lactic acid strain is preferably heat-treated lactic acid bacteria in terms with fermentation period. The heat-treatment is carried out by placing the cold-stored strain in an incubator and incubating the strain till a temperature ranging 25–40° C.

In step c), while maintaining the temperature of the incubator within the range of 35–40° C., culturing is carried out for 3–20 hours. In case that the heat-treated lactic acid strain is inoculated, the culture period is preferably for within the range of 3–6 hours.

In step d), aging is carried out at a temperature ranging 3–5° C. for a predetermined time.

The present invention also provides a lactic acid fermented solution of mushroom produced by the said method for preparing the lactic acid fermented solution of mushroom.

The property of lactic acid fermented solution of mushroom thus obtained, inhibitory effect against the formation of peroxidized lipid, and dropping effect on blood sugar level are investigated

*Agaricus blazei, Ganderma lucidum, Pleurotus osteratus. Agaricus bisporus, Flammulina velutipes, Grifola frondosa, Lentinus edodes, Elfvingia applanata* and *Crdyceps* spp. are used to lactic acid fermented solution of mushroom according to the present invention, but the scope of the invention is not limited to them. All of the edible and medicinal mushrooms can be used for preparing the lactic acid fermented solution of mushroom according to the present invention.

First, with reference to FIG. 1, the method for preparing the lactic acid fermented solution of mushroom according to the present invention is schematically explained.

a) Step of Preparing a Mushroom Ingredients-Containing Medium i) Obtaining Mushroom Ingredients One or more parts among the fruit bodies and mycelia of mushroom *Agaricus blazei, Ganderma lucidum, Grifola frondosa* and *Elfvingia applanata,* and fruit bodies of *Pleurotus osteratus, Agaricus bisporus, Flammulina velutipes, Lentinus edodes* and *Crdyceps* spp. were selected, washed, dried in hot-air drier at a temperature of 60° C. and ground to obtain a dried powder of mushroom.

One or more parts among the fruit bodies and mycelia of mushroom *Agaricus blazei, Ganderma lucidum, Grifola frondosa* and *Elfvingia applanata,* and fruit bodies of *Pleurotus osteratus, Agaricus bisporus, Flammulina velutipes,* *Lentinus edodes* and *Crdyceps* spp. were selected, washed, and extracted in high-pressured sterilizer using appropriated solvent in a conventional manner to obtain a mushroom extract.

ii) Preparing a Lactic Acid Bacteria Medium

The medium was prepared by adding 0.1–10% by weight of the obtained mushroom ingredients, 1–50% by weight, preferably 1–20% by weight of defatted milk, 0.1–20% by weight of sugar and the balance of purified water to the mushroom ingredients-containing medium obtained in said i) and homogenizing the mixture to prepare a lactic acid bacteria medium. Other effective components such as oligosaccharide, dextrin, vitamin and mineral can be further included in the lactic acid bacteria medium.

iii–iv) Heat-Treating and Cooling

After heat-treating the ingredients-containing medium of mushroom at a temperature ranging 75–110° C. for 15–40 minutes, the heat-treated medium was cooled to temperature ranging 35–40° C.

b) Step of Inoculating Lactic Acid Strain Onto the Medium

Lactic acid bacteria in cold storage or heat-treated lactic acid bacteria incubated to a temperature ranging 25° C. to 40° C. in an incubator was inoculated onto the medium cooled in iv) of the step a). At this time, the amount of the inoculated lactic acid strain can be selected within the range of 1–10% by weight, based on the total weight of said mushroom ingredients-containing medium.

c) Step of Culturing the Strain-Inoculated Medium

While maintaining the temperature of 35–40° C. in an incubator, lactic acid bacteria medium inoculated with strain was cultured for 3–20 hours. In case that the heat-treated lactic acid strain was inoculated, the culture period was preferably within the range of 3–6 hours.

d) Step of Aging the Cultured Medium.

Strain cultured in said step c) was aged at a temperature ranging 3–5° C. for 10–20 hours.

Hereinafter, the preferred embodiments of the present invention will be described, but the preferred embodiments are intended only for the purpose of an illustrative, and the present invention is not limited thereto.

EXAMPLE

Material

Mycelia of *Agaricus blazei, Ganderma lucidum, Grifola frondosa, Elfvingia applanata, Pleurotus osteratus, Agaricus bisporus, Flammulina velutipes, Lentinus edodes* and *Crdyceps* spp. were cultured in laboratory room, and fruit bodies of *Agaricus blazei, Ganderma lucidum, Grifola frondosa* and *Elfvingia applanata* were obtained from market.

Examples 1–4

Preparation of Lactic Acid Fermented Solution of *Agaricus blazei*

Example 1

Fruit bodies and mycelia of *Agaricus blazei* were ground to obtain a dried powder. A mixture of 5% by weight of the obtained powder, 10% by weight of defatted milk, 2% by weight of sugar and the balance of purified water was added to a medium and homogenized. The mushroom ingredients-containing medium was subject to heat-treatment at a temperature of 100° C. for 20 minutes and then cooled to 37° C.

3% by weight of *Lactobacillus bulgaricus,* based on the total weight of said mushroom ingredients-containing medium, in cold storage was inoculated onto the medium. Six samples of the strain-inoculated mushroom ingredients-containing medium were prepared. While maintaining the temperature of the incubator to 37° C., the samples were cultured for 1, 2, 3, 4, 5 and 6 hours, respectively, and their pH and acidity were measured. Subsequently, the cultured samples were aged at a temperature of 4° C. for 12 hours. The aged samples were homogenized with homogenizer to prepare a lactic acid fermented solution of *Agaricus blazei*.

Example 2

Lactic acid fermented solution of *Agaricus blazei* was prepared according to the same procedure as Example 1 except that the *Agaricus blazei* extract was used instead of the dried powder.

Example 3

Fruit bodies and mycelia of *Agaricus blazei* were ground to obtain a dried powder. A mixture of 5% by weight of the obtained powder, 10% by weight of defatted milk, 2% by weight of sugar and the balance of purified water was added to a medium and homogenized. The mushroom ingredients-containing medium was subject to heat-treatment at a temperature of 100° C. for 20 minutes and then cooled to 37° C.

*Lactobacillus bulgaricus* in cold storage was incubated to a temperature of 37° C. for 1 hour in an incubator.

3% by weight of the incubated *Lactobacillus bulgaricus*, based on the total weight of said mushroom ingredients-containing medium, was inoculated onto the medium. Six samples of the strain-inoculated mushroom ingredients-containing medium were prepared. While maintaining the temperature of the incubator to 37° C., the samples were cultured for 1, 2, 3, 4, 5 and 6 hours, respectively, and their pH and acidity were measured. Subsequently, the cultured samples were aged at a temperature of 4° C. for 12 hours. The aged samples were homogenized with homogenizer to prepare a lactic acid fermented solution of *Agaricus blazei*.

Example 4

Lactic acid fermented solution of *Agaricus blazei* was prepared according to the same procedure as Example 3 except that *Agaricus blazei* extract was used instead of the dried powder.

Examples 5–8

Preparation of Lactic Acid Fermented Solution of *Ganderma lucidum*

Example 5

Lactic acid fermented solution of *Ganderma lucidum* was prepared according to the same procedure as Example 1 except that *Ganderma lucidum* was used instead of *Agaricus blazei*.

Example 6

Lactic acid fermented solution of *Ganderma lucidum* was prepared according to the same procedure as Example 2 except that *Ganderma lucidum* was used instead of *Agaricus blazei*.

Example 7

Lactic acid fermented solution of *Ganderma lucidum* was prepared according to the same procedure as Example 3 except that *Ganderma lucidum* was used instead of *Agaricus blazei*.

Example 8

Lactic acid fermented solution of *Ganderma lucidum* was prepared according to the same procedure as Example 4 except that *Ganderma lucidum* was used instead of *Agaricus blazei*.

Examples 9–12

Preparation of Lactic Acid Fermented Solution of *Pleurotus osteratus*

Example 9

Lactic acid fermented solution of *Pleurotus osteratus* was prepared according to the same procedure as Example 1 except that the fruit bodies of *Pleurotus osteratus* were used instead of the fruit bodies and mycelia of *Agaricus blazei*.

Example 10

Lactic acid fermented solution of *Pleurotus osteratus* was prepared according to the same procedure as Example 2 except that the fruit bodies of *Pleurotus osteratus* were used instead of the fruit bodies and mycelia of *Agaricus blazei*.

Example 11

Lactic acid fermented solution of *Pleurotus osteratus* was prepared according to the same procedure as Example 3 except that the fruit bodies of *Pleurotus osteratus* were used instead of the fruit bodies and mycelia of *Agaricus blazei*.

Example 12

Lactic acid fermented solution of *Pleurotus osteratus* was prepared according to the same procedure as Example 4 except that the fruit bodies of *Pleurotus osteratus* were used instead of the fruit bodies and mycelia of *Agaricus blazei*.

Examples 13–16

Preparation of Lactic Acid Fermented Solution of *Agaricus bisporus*

Example 13

Lactic acid fermented solution of *Agaricus bisporus* was prepared according to the same procedure as Example 1 except that the fruit bodies of *Agaricus bisporus* were used instead of the fruit bodies and mycelia of *Agaricus blazei*.

Example 14

Lactic acid fermented solution of *Agaricus bisporus* was prepared according to the same procedure as Example 2 except that the fruit bodies of *Agaricus bisporus* were used instead of the fruit bodies and mycelia of *Agaricus blazei*.

Example 15

Lactic acid fermented solution of *Agaricus bisporus* was prepared according to the same procedure as Example 3 except that the fruit bodies of *Agaricus bisporus* were used instead of the fruit bodies and mycelia of *Agaricus blazei*.

Example 16

Lactic acid fermented solution of *Agaricus bisporus* was prepared according to the same procedure as Example 4 except that the fruit bodies of *Agaricus bisporus* were used instead of the fruit bodies and mycelia of *Agaricus blazei*.

Examples 17–20

Preparation of Lactic Acid Fermented Solution of *Flammulina velutipes*

Example 17

Lactic acid fermented solution of *Flammulina velutipes* was prepared according to the same procedure as Example 1 except that the fruit bodies of *Flammulina velutipes* were used instead of the fruit bodies and mycelia of *Agaricus blazei*.

Example 18

Lactic acid fermented solution of *Flammulina velutipes* was prepared according to the same procedure as Example 2 except that the fruit bodies of *Flammulina velutipes* were used instead of the fruit bodies and mycelia of *Agaricus blazei*.

Example 19

Lactic acid fermented solution of *Flammulina velutipes* was prepared according to the same procedure as Example 3 except that the fruit bodies of *Flammulina velutipes* were used instead of the fruit bodies and mycelia of *Agaricus blazei*.

Example 20

Lactic acid fermented solution of *Flammulina velutipes* was prepared according to the same procedure as Example 4 except that the fruit bodies of *Flammulina velutipes* were used instead of the fruit bodies and mycelia of *Agaricus blazei*.

Examples 21–24

Preparation of Lactic Acid Fermented Solution of *Grifola frondosa*

Example 21

Lactic acid fermented solution of *Grifola frondosa* was prepared according to the same procedure as Example 1 except that *Grifola frondosa* was used instead of *Agaricus blazei*.

Example 22

Lactic acid fermented solution of *Grifola frondosa* was prepared according to the same procedure as Example 2 except that *Grifola frondosa* was used instead of *Agaricus blazei*.

Example 23

Lactic acid fermented solution of *Grifola frondosa* was prepared according to the same procedure as Example 3 except that *Grifola frondosa* was used instead of *Agaricus blazei*.

Example 24

Lactic acid fermented solution of *Grifola frondosa* was prepared according to the same procedure as Example 4 except that *Grifola frondosa* was used instead of *Agaricus blazei*.

Examples 25–28

Preparation of Lactic Acid Fermented Solution of *Lentinus edodes*

Example 25

Lactic acid fermented solution of *Lentinus edodes* was prepared according to the same procedure as Example 1 except that the fruit bodies of *Lentinus edodes* were used instead of the fruit bodies and mycelia of *Agaricus blazei*.

Example 26

Lactic acid fermented solution of *Lentinus edodes* was prepared according to the same procedure as Example 2 except that the fruit bodies of *Lentinus edodes* were used instead of the fruit bodies and mycelia of *Agaricus blazei*.

Example 27

Lactic acid fermented solution of *Lentinus edodes* was prepared according to the same procedure as Example 3 except that the fruit bodies of *Lentinus edodes* were used instead of the fruit bodies and mycelia of *Agaricus blazei*.

Example 28

Lactic acid fermented solution of *Lentinus edodes* was prepared according to the same procedure as Example 4 except that the fruit bodies of *Lentinus edodes* were used instead of the fruit bodies and mycelia of *Agaricus blazei*.

Examples 29–32

Preparation of Lactic Acid Fermented Solution of *Elfvingia applanata*

Example 29

Lactic acid fermented solution of *Elfvingia applanata* was prepared according to the same procedure as Example 1 except that *Elfvingia applanata* was used instead of *Agaricus blazei*.

Example 30

Lactic acid fermented solution of *Elfvingia applanata* was prepared according to the same procedure as Example 2 except that *Elfvingia applanata* was used instead of *Agaricus blazei*.

Example 31

Lactic acid fermented solution of *Elfvingia applanata* was prepared according to the same procedure as Example 3 except that *Elfvingia applanata* was used instead of *Agaricus blazei*.

Example 32

Lactic acid fermented solution of *Elfvingia applanata* was prepared according to the same procedure as Example 4 except that *Elfvingia applanata* was used instead of *Agaricus blazei*.

Examples 33–36

Preparation of Lactic Acid Fermented Solution of *Crdyceps* spp.

Example 33

Lactic acid fermented solution of *Crdyceps* spp. was prepared according to the same procedure as Example 1 except that the fruit bodies of *Lentinus edodes* were used instead of the fruit bodies and mycelia of *Crdyceps* spp.

Example 34

Lactic acid fermented solution of *Crdyceps* spp. was prepared according to the same procedure as Example 2 except that the fruit bodies of *Lentinus edodes* were used instead of the fruit bodies and mycelia of *Crdyceps* spp.

Example 35

Lactic acid fermented solution of *Crdyceps* spp. was prepared according to the same procedure as Example 3 except that the fruit bodies of *Lentinus edodes* were used instead of the fruit bodies and mycelia of *Crdyceps* spp.

Example 36

Lactic acid fermented solution of *Crdyceps* spp. was prepared according to the same procedure as Example 4 except that the fruit bodies of *Lentinus edodes* were used instead of the fruit bodies and mycelia of *Crdyceps* spp Example 37

Preparation of Lactic Acid Fermented Solution of *Pleurotus osteratus*

Lactic acid fermented solution of *Pleurotus osteratus* was prepared according to the same procedure as Example 1 except that a mixture of 1% by weight of the dried powder and 1% by weight of the extract obtained from the fruit bodies and mycelia of *Pleurotus osteratus* was used instead of the dried powder obtained from the fruit bodies and mycelia of *Agaricus blazei*.

Example 38

Preparation of Lactic Acid Fermented Solution of *Ganderma lucidum*

Lactic acid fermented solution of *Ganderma lucidum* was prepared according to the same procedure as Example 1 except that a mixture of 0.1% by weight of the dried powder and 5.0% by weight of the extract obtained from the fruit bodies and mycelia of *Ganderma lucidum* was used instead of the dried powder obtained from the fruit bodies and mycelia of *Agaricus blazei*.

Example 39

Preparation of Lactic Acid Fermented Solution of Mixed Mushrooms

A mixture of 1% by weight of the dried powder and 1% by weight of the extract obtained from *Lentinus edodes*, *Pleurotus osteratus* and *Ganderma lucidum* (weight ratio= 4:4:2), 13% by weight of defatted milk, 10% by weight of oligosaccharide, 1% by weight of dextrin and 74% by weight of purified water was homogenized to produce a mushroom ingredients-containing medium. The produced mushroom ingredients-containing medium was sterilized by heating at a temperature of 80° C. for 30 minutes and then cooled to 37° C. Onto the lactic acid bacteria culturing medium thus obtained was inoculated *Lactobacillus bulgaricus* in an amount of 3% by weight based on the total weight of said mushroom ingredients-containing medium. The medium was cultured in an incubator at a temperature of 37° C. for 12 hours, and then aged at a temperature of 4° C. for 12 hours. The aged medium was homogenized with homogenizer to prepare a lactic acid fermented solution of the mixed mushrooms.

Examples 40–42. Comparative Examples 1 and 2

Preparation of Lactic Acid Fermented Solution of *Ganderma lucidum*

About 1000 ml (to 10% of the total weight) of distilled water was added to 100 g of *Ganderma lucidum*, and extract using high-pressured sterilizer at a lower temperature than 100° C. for 1 hour. The obtained extract was filtered, 100 ml of distilled water was added thereto, and extracted at a higher temperature of 121° C. for 1 hour again to obtain a *Ganderma lucidum* extract.

0.01% by weight (Comparative Example 1), 0.1% by weight (Example 40), 0.5% by weight (Example 41), 5% by weight (Example 42) and 10% by weight (Comparative Example 2), respectively, of the obtained *Ganderma lucidum* extract, based on the total weight of each medium, were added to each medium consisting of 8% by weight of defatted milk, 10% by weight of oligosaccharide, 1% by weight of dextrin and the balance of purified water medium, and homogenized.

3% by weight of *Lactobacillus bulgaricus*, based on the total weight of said mushroom ingredients-containing medium, was inoculated onto each medium. While maintaining the temperature of the incubator to 37° C., the each medium was cultured for 12 hours and aged at a temperature of 4° C. for 12 hours to obtain lactic acid fermented solutions of *Ganderma lucidum*

EXPERIMENTAL EXAMPLE

Experimental Example 1 pH, Acidity and Rheology

To measure pH, acidities and rheologies (hardness, breaking energy, elastic molecule) of lactic acid fermented solutions of mushrooms obtained from Examples 1–36 over the culture period, samples of lactic acid fermented solutions obtained from each Example were homogenized with a homogenizer at 1000 rpm for 30 seconds.

The measurement of pH was carried out with a pH meter, and the measurement of acidity was carried out by taking a portion (10 ml) of each lactic acid fermented solution of mushrooms, diluting with tertiary distilled water at a ratio of 1:1, adding 0.1% phenolphthalein solution thereto and titrating with 0.1 N NaOH.

Experimental Result

As shown in Tables 1 and 2, lactic acid fermented solutions of mushrooms obtained from Examples 1–36 had low pH and high acidities. Also, as depicted in FIGS. 2–5, effective rate of formation of lactic acid was guarantied and rheologies of hardness, breaking energy and elastic molecule showed soft tissue and excellent properties (e.g., viscosity).

In particular, as shown in Table 2, in case that heat-treated lactic acid bacteria were inoculated onto the mushroom ingredients-containing media, fermentation periods were shortened by about 33%.

TABLE 1 pH and acidities of lactic acid fermented solutions of mushrooms

| | PH/acidity | | | | | | |
|---|---|---|---|---|---|---|---|
| | 1 | 3 | 6 | 9 | 12 | 15 | 16 |
| Example 1  | 6.6/0.15 | 6.2/0.25 | 5.8/0.36 | 5.6/0.41 | 5.1/0.59 | 4.6/0.74 | 4.3/0.84 |
| Example 2  | 6.6/0.15 | 6.2/0.24 | 5.7/0.38 | 5.5/0.44 | 4.9/0.61 | 4.6/0.73 | 4.2/0.87 |
| Example 5  | 6.6/0.15 | 6.1/0.28 | 5.7/0.39 | 5.5/0.43 | 4.9/062  | 4.6/0.74 | 4.4/0.83 |
| Example 6  | 6.6/0.15 | 6.1/0.27 | 5.8/0.35 | 5.4/0.47 | 4.8/0.66 | 4.5/0.79 | 4.3/0.85 |
| Example 9  | 6.6/0.15 | 6.0/0.30 | 5.7/0.39 | 5.4/0.47 | 4.9/0.62 | 4.7/0.70 | 4.5/0.80 |
| Example 10 | 6.6/0.15 | 6.2/0.30 | 5.8/0.36 | 5.5/0.43 | 4.9/0.61 | 4.6/0.72 | 4.4/0.83 |
| Example 13 | 6.6/0.15 | 6.2/0.25 | 5.7/0.38 | 5.4/0.46 | 4.9/0.60 | 4.6/0.73 | 4.3/0.86 |
| Example 14 | 6.6/0.15 | 6.1/0.27 | 5.7/0.38 | 5.4/0.46 | 4.8/0.66 | 4.6/0.72 | 4.4/0.83 |
| Example 17 | 6.6/0.15 | 6.2/0.24 | 5.7/0.39 | 5.4/0.47 | 4.9/0.62 | 4.6/0.74 | 4.4/0.83 |
| Example 18 | 6.6/0.15 | 6.2/0.24 | 5.8/0.39 | 5.5/0.44 | 4.9/0.62 | 4.7/0.70 | 4.5/0.80 |
| Example 21 | 6.6/0.14 | 6.0/0.29 | 5.7/0.39 | 5.3/0.50 | 4.7/0.70 | 4.5/0.80 | 4.2/0.89 |
| Example 22 | 6.6/0.15 | 6.2/0.25 | 5.9/0.33 | 5.5/0.44 | 4.8/0.66 | 4.6/0.74 | 4.3/0.86 |
| Example 25 | 6.6/0.15 | 6.0/0.30 | 5.7/0.38 | 5.3/0.49 | 4.8/0.65 | 4.6/0.74 | 4.4/0.82 |
| Example 26 | 6.6/0.15 | 6.1/0.28 | 5.8/0.35 | 5.4/0.45 | 4.8/0.65 | 4.6/0.73 | 4.4/0.81 |
| Example 29 | 6.6/0.15 | 6.3/0.23 | 5.8/0.35 | 5.5/0.44 | 4.9/0.62 | 4.6/0.74 | 4.4/0.82 |
| Example 30 | 6.6/0.15 | 6.2/0.25 | 5.9/0.32 | 5.6/0.40 | 4.9/0.62 | 4.6/0.72 | 4.5/0.79 |
| Example 33 | 6.6/0.15 | 6.2/0.24 | 5.9/0.31 | 5.5/0.44 | 4.8/0.66 | 4.6/0.73 | 4.4/0.83 |
| Example 34 | 6.6/0.15 | 6.2/0.25 | 5.9/0.33 | 5 6/0.41 | 4.8/0.65 | 4.7/0.70 | 4.4/0.81 |

TABLE 2 pH and acidities of lactic acid fermented solutions of mushrooms

| | PH/acidity | | | | | | |
|---|---|---|---|---|---|---|---|
| | 0 | 1 | 2 | 3 | 4 | 5 | 6 |
| Example 3  | 6.6/0.15 | 6.3/0.23 | 6.1/0.27 | 5.8/0.36 | 5.1/0.56 | 4.8/0.66 | 4.6/0.74 |
| Example 4  | 6.6/0.15 | 6.2/0.25 | 6.1/0.27 | 5.7/0.39 | 5.2/0.52 | 4.8/0.65 | 4.6/0.71 |
| Example 7  | 6.6/0.15 | 6.4/0.21 | 6.2/0.25 | 5.8/0.34 | 5.0/0.58 | 4.7/0.70 | 4.6/0.71 |
| Example 8  | 6.6/0.15 | 6.4/0.20 | 6.2/0.24 | 5.9/0.33 | 5 1/0.55 | 4.7/0.68 | 4.6/0.72 |
| Example 11 | 6.6/0.15 | 6.3/0.23 | 6.1/0.26 | 5.8/0.35 | 5.0/0.57 | 4.7/0.67 | 4.7/0.70 |
| Example 12 | 6.6/0.15 | 6.4/0.21 | 6.2/0.24 | 5.9/0.31 | 5.2/0.52 | 4.8/0.65 | 4.6/0.74 |
| Example 15 | 6.6/0.15 | 6.4/0.19 | 6.2/0.25 | 6.0/0.30 | 5.3/0.50 | 4.9/0.61 | 4.7/0.70 |
| Example 16 | 6.6/0.15 | 6.5/0.17 | 6.2/0.25 | 6.0/0.29 | 5.4/0.47 | 4.9/0.61 | 4.7/0.69 |
| Example 19 | 6.6/0.15 | 6.5/0.18 | 6.2/0.25 | 5.9/0.31 | 5.3/0.49 | 5.0/0.59 | 4.7/0.70 |
| Example 20 | 6.6/0.15 | 6.5/0.17 | 6.2/0.24 | 5.9/0.31 | 5.4/0.46 | 5.0/0.57 | 4.7/0.68 |
| Example 23 | 6.6/0.14 | 6.2/0.24 | 6.0/0.30 | 5.8/0.36 | 5.3/0.50 | 5.0/0.59 | 4.7/0.68 |
| Example 24 | 6.6/0.15 | 6.1/0.26 | 5.9/0.32 | 5.8/0.34 | 5.3/0.49 | 5.0/0.57 | 4.5/0.79 |
| Example 27 | 6.6/0.15 | 6.4/0.19 | 6.1/0.27 | 5.7/0.39 | 5.2/0.25 | 4.8/0.64 | 4.5/0.76 |
| Example 28 | 6.6/0.15 | 6.5/0.17 | 6.3/0.23 | 5.9/0.33 | 5.3/0.50 | 4.9/0.60 | 4.6/0.73 |
| Example 31 | 6.5/0.14 | 6.4/0.21 | 6.2/0.25 | 5.9/0.33 | 5.6/0.41 | 5.1/0.56 | 4.8/0.66 |
| Example 32 | 6.6/0.15 | 6.5/0.18 | 6.2/0.25 | 6.0/0.30 | 5.3/0.50 | 4.9/0.62 | 4.7/0.69 |
| Example 35 | 6.5/0.16 | 6.2/0.25 | 5.9/0.32 | 5.7/0.38 | 5.3/0.49 | 5.0/0.59 | 4.6/0.74 |
| Example 36 | 6.6/0.16 | 6.3/0.22 | 5.9/0.33 | 5.6/0.40 | 5.2/0.52 | 4.9/0.60 | 4.5/0.75 |

Experimental Example 2

Inhibitory Effect of Peroxidized Lipid Formation

To investigate the influence of lactic acid fermented solution of mushroom according to the present invention on peroxidized lipid, lactic acid bacteria fermented milk, a mixed powder of *Lentinus edodes, Pleurotus ostreatus* and *Ganoderma lucidum*, and lactic acid fermented solution of mushroom obtained in Example 39 were added to cholesterol-containing diet, respectively.

For 4 weeks from the addition, the influences on peroxidized lipid in female rats were investigated in vivo.
① Material
The dried products of *Lentinus edodes, Ganoderma lucidum* and *Pleurotus ostreatus* were obtained from Jinju Mushroom Agricultural Association. The dried products were cut to pieces, ground and pulverized to obtain a powder in the form of fine particles passing a screen of 20 mesh.
② Experimental Animal, Condition and Diet Composition Female white rats (Sprague Dawley) weighing about 180 g as experimental animals were grown in a condition of temperature 22±2° C., relative humidity 50±5% and under light (07:00–19:00) and darkness at 12 hour intervals. Feed in the form of solid diet was provided for 1 week and then with normal feed for 4 days. The rats were divided into 5 groups, by 6 rats per one group.

Experimental diet groups consist of normal diet group (ND), cholesterol diet group (CD) (which is obtained by adding 0.5%(w/w) of cholesterol and 0.125% (w/w) of sodium cholate to the normal diet group), lactic acid bacteria fermented milk-supplemented group (CDFM) (which is obtained by adding lactic acid bacteria fermented milk to the cholesterol diet), mushroom powder-supplemented group (CDMP) (which is obtained by adding mushroom powder to the cholesterol diet), and lactic acid fermented solution of mushroom-supplemented group (CDFMMP) (which is obtained by adding lactic acid fermented solution of mushroom to cholesterol diet). At this time, mushroom powder of CDMP group was a mixture of *Lentinus edodes, Pleurotus*

*osteratus* and *Ganderma lucidum* and the mixture was added in an amount of 4% to the group. In CDFM group, lactic acid bacteria fermented milk, which is prepared by culturing at a temperature of 30° C. for 12 hours using *Lactobacillus bulgaricus* and by lyophilizing, was added in an amount of 13.5% to the diet. In CDFMMP group, lactic acid bacteria fermented milk, which is prepared by adding a mixture of *Lentinus edodes, Pleurotus osteratus* and *Ganderma lucidum* at a ratio of 4:4:2 to a *Lactobacillus bulgaricus* cultured solution in an amount of 4%, by culturing at a temperature of 30° C. for 12 hours and by lyophilizing, was added in an amount of 17.5% to the diet. Experimental diet compositions of these experimental diet groups were shown in Table 3. Experimental diets and drink were freely fed for 4 weeks. Diet feeding amounts were monitored at fixed time every day, and their weights were measured once per a week.

TABLE 3

Diet composition

| | ND | CD | CDFM | CDME | CDFMMP |
|---|---|---|---|---|---|
| Casein | 20.0 | 20.0 | 20.0 | 20.0 | 20.0 |
| ,-Corn starch | 15.0 | 15.0 | 15.0 | 15.0 | 15.0 |
| Soybean oil | 10.0 | 10.0 | 10.0 | 10.0 | 10.0 |
| Cellulose | 5.0 | 5.0 | 5.0 | 5.0 | 5.0 |
| AIN-93 Mineral Mixture | 4.0 | 4.0 | 4.0 | 4.0 | 4.0 |
| AIN-93 Vitamin Mixture | 1.0 | 1.0 | 1.0 | 1.0 | 1.0 |
| L-Methionine | 0.3 | 0.3 | 0.3 | 0.3 | 0.3 |
| Choline bitartrate | 0.2 | 0.2 | 0.2 | 0.2 | 0.2 |
| Cholesterol | 0.0 | 0.5 | 0.5 | 0.5 | 0.5 |
| Sodium cholate | 0 | 0.125 | 0.125 | 0.125 | 0.125 |
| Fermented milk (FM) | 0 | 0 | 13.5 | 0 | 0 |
| Mushroom extracts (ME) | 0 | 0 | 0 | 4.0 | 0 |
| Lactic acid Fermented Solution of mushroom | 0 | 0 | 0 | 0 | 17.5 |
| Sucrose | balance | | | | | in which
ND: normal diet group
CD: cholesterol diet group
CDFM: lactic acid bacteria fermented milk-supplemented group to the cholesterol diet group
CDME: the mushroom extact-supplemented group to the cholesterol diet group
CDFMME: lactic acid fermented solution of mushroom-supplemented group to the cholesterol diet group ③ Sample At the final experimental day, the experimental animals were fasted for 12 hours, put under slight anesthesia with ether and then taken blood from the inferior vena cava. This blood was centrifuged at room temperature for 15 under 3,000 rpm to obtain sera. The incised tissue was washed with cold 0.9% physiological saline water, dried, and weighed to obtain a sample for analyzing the concentration of peroxidized lipid.

④ Analyses of Serum, Liver Lipid and Blood Sugar Level

Total cholesterol in serum was measured using Cholesterol C-test wako kit (Wako Junyaku, Osaka, Japan), HDL-cholesterol in serum was measured using HDL-cholesterol E-test wako kit (Wako Junyaku, Osaka, Japan), neutral lipid in serum was measured using Triglyceride E-test wako kit (Wako Junyaku, Osaka, Japan), phospholipid in serum was measured using Phospholipid C-test wako kit (Wako Junyaku, Osaka, Japan), the concentration of glucose in serum was measured using commercially available kit (Wako Junyaku, Osaka, Japan) in accordance with glucose oxidase method, and lipid in liver tissue was extracted in accordance with Folch's method and the concentration thereof was measured the same method as lipid in serum.

⑤ Homogenate, Microsome and Mitochondria Fraction of Each Tissue 1.15% KC1–10 mM phosphate buffer (pH 7.4) was added to each incised tissue, and then homogenized using homogenizer. A part of the solution was taken as a homogenate fraction, and a microsome fraction and mitochondria fraction were separated from the remaining solution, respectively.

⑥ Measurement of the Concentration of Peroxidized Lipid in Tissue Fraction

The concentration of the peroxidized lipid in each tissue was carried out the following method. First, 2 ml of thiobarbituric acid (TBA) reagent was added to 1 ml of homogenate, microsome and mitochondria fraction solution, respectively, and mixed well. The mixture was heated in water bath for 15 minutes, cooled, and centrifuged at 3,000 rpm for 15 minutes.

The supernatant was taken and measured absorbance at 535 nm. The concentration of peroxidized lipid in tissue was expressed as nmol/g of malondialdehyde.

⑦ Statistics

ALT and AST values in the sera were measured using blood chemistry analyzer (Vitalab, Spectra II, Merck). The statistical significance for the test result of each group was examined based on Student's t-test, and the result was recognized as having a statistical significance when its P value is less than 5%.

The experimental result was expressed as an average value and standard error through one-way ANOVA, the statistical significance for the experimental result of each group was examined based on Duncan's multiple range test, and the result was recognized as having a statistical significance when its P value is less than 5%.

⑧ Result (1) Change in Concentration of Serum Lipid

The change in concentration of serum lipid was shown in Table 4.

TABLE 4

The concentration of lipid and glucose in blood plasma of experimental animal

| | | ND | CD | CDFM | CDME | CDFMMP |
|---|---|---|---|---|---|---|
| Lipid in serum | Total Cholesterol | 60.49 ± 8.11 | 279.93 ± 45.62 | 155.07 ± 18.60 | 123.77 ± 18.55 | 80.41 ± 9.01 |
| | HDL-Cholesterol | 42.25 ± 5.79 | 16.55 ± 0.88 | 19.14 ± 1.88 | 38.55 ± 1.69 | 41.25 ± 5.99 |
| | Triglyceride | 138.17 ± 4.52 | 127.28 ± 2.94 | 113.34 ± 2.69 | 135.12 ± 2.56 | 128.47 ± 2.65 |
| | Phospholipid | 101.32 ± 9.16 | 131.66 ± 12 14 | 87.80 ± 11.80 | 101.76 ± 8.31 | 97.42 ± 6.52 |

TABLE 4-continued

The concentration of lipid and glucose in
blood plasma of experimental animal

|  | ND | CD | CDFM | CDME | CDFMMP |
|---|---|---|---|---|---|
| Lipid in Total Cholesterol serum | 60.49 ± 8.11 | 279.93 ± 45.62 | 155.07 ± 18.60 | 123.77 ± 18.55 | 80.41 ± 9.01 |
| AI1 | 0.34 ± 0.03 | 15.91 ± 1 71 | 7 10 ± 0 49 | 2.53 ± 0.06 | 0.89 ± 0.06 |
| Serum glucose level (mg/100 ml) | 93.57 ± 8.23 | 100.11 ± 4.23 | 81.18 ± 9.69 | 93.45 ± 4.63 | 97.63 ± 11.98 | in which
the values mean average ± SE for 6 rats per one group.
Atherogenic index (AI) means total cholesterol - HDL cholesterol/HDL cholesterol, and the values having different characters have statistical significance of $p < 0.05$.

As known from Table 4, the concentration of total cholesterol in serum was increased by 4.6 times in cholesterol diet group (CD) when compared with normal diet group (ND). This suggests high cholesterol hyperglycemia. However, the concentration of total cholesterol was decreased by 44.6% in lactic acid bacteria fermented milk-supplemented group (CDFM), 57.4% in mushroom extract-supplemented group (CDMP) and 72.0% in lactic acid fermented solution of mushroom-supplemented group (CDFMMP) when compared with the cholesterol diet group (CD).

The concentration of HDL-cholesterol in serum was increased in CDMP and CDFMMP groups, but has no change in CDFM. Furthermore, the increase was remarkable in CDFMMP group relative to CDMP group. From this result, it seems that lactic acid bacteria have physiologically active ingredients for increasing the concentration of HDL-cholesterol.

According to Framinghan Heart study, when arteriosclerosis index is not more than 3.5, it is safe from the occurrence of coronary artery diseases. Further, the study recommends the index should be maintained to be not more than 4.5.

In Table 3, comparing arteriosclerosis indices between experimental groups, arteriosclerosis index in cholesterol diet group (CD) was remarkably increased, compared to the normal diet group (ND). And, arteriosclerosis index in cholesterol diet group (CD) was slightly decreased, compared to the lactic acid bacteria fermented milk-supplemented group (CDFM). However, in the mushroom extract-supplemented group (CDMP) and in lactic acid fermented solution of mushroom-supplemented group (CDFMMP), their arteriosclerosis indices were decreased by 68.4% and 83.3%, respectively.

(2) The Formation of the Peroxidized Lipid in Biomembrane

Lipid peroxidation in biomembrane is caused by the increased formation of free radical due to oxidative stress in tissue cells and by the decreased antioxidative defense power in a living body. The TBARS levels showing the formation degree of biomembrane peroxidized lipid in animal are enumerated in Table 5.

TABLE 5

TBARS levels in female rats tissue (nmol/g of tissue)

| Ingredients | ND | CD | CDFM | CDMP | CDFMMP |
|---|---|---|---|---|---|
| Liver | 117.74 ± 4.71[a] | 121.45 ± 3.43[a] | 102.15 ± 9 52[b] | 123 37 ± 10.28[a] | 99.07 ± 5.68[b] |
| Heart | 25.50 ± 0.37[a] | 24.27 ± 0.42[ab] | 24.16 ± 0 56[ab] | 24.17 ± 0.53[ab] | 23.55 ± 0.67[b] |
| Kidney | 14.52 ± 0.35[a] | 27.42 ± 0.71b | 22.75 ± 2.70[c] | 28.34 ± 0.48[b] | 26.52 ± 1.12[b] |
| Spleen | 13.74 ± 0.43 | 13.64 ± 0.42 | 13.95 ± 0.73 | 14 60 ± 0.51 | 14.28 ± 0.65 |

Table 5 revealed that the relative contents of peroxidized lipid in each tissue were found in liver, kidney, heart and spleen in sequence in the normal diet group and cholesterol diet group. However, in case that male rats were freely fed with cholesterol diet for 4 weeks, the relative contents of TBARS in each tissue were found in brain, kidney, heart, liver and spleen in sequence. Also in case that male rats (6 months old) were fed with normal diet, the relative contents of TBARS in each tissue were found in heart liver, brain and kidney in sequence. These results suggested that the formation of peroxidized lipid in tissue depended on the differences between species, age, and diet composition.

Experimental Example 3

The Dropping Effect of Serum Glucose Level

① Method

To examine the influence of lactic acid fermented solution of mushroom on the drop of serum glucose level, the following method was performed in patients with diabetes mellitus. First, 10 men (age of 25–67, average age of 45) having hyperglycemia (average: 315 mg/dL) from normal diet group were selected, and fed with normal diet for 3 weeks. The measurement of serum glucose level was performed at seven before meals. The results were listed in the following Table 6.

TABLE 6

The change of serum glucose level (mg/dL)
in patients with diabetes mellitus as a control group

| Patients | \multicolumn{11}{c}{Days} |
|---|---|---|---|---|---|---|---|---|---|---|---|
|  | 1 | 3 | 5 | 7 | 9 | 11 | 13 | 15 | 17 | 19 | 21 |
| 1 | 342 | 279 | 224 | 275 | 262 | 371 | 197 | 246 | 299 | 303 | 307 |
| 2 | 295 | 324 | 333 | 287 | 288 | 350 | 401 | 370 | 368 | 362 | 355 |
| 3 | 378 | 410 | 420 | 387 | 195 | 394 | 338 | 382 | 442 | 351 | 400 |
| 4 | 254 | 382 | 358 | 299 | 308 | 412 | 382 | 172 | 302 | 296 | 289 |
| 5 | 324 | 192 | 392 | 373 | 392 | 158 | 381 | 254 | 325 | 285 | 244 |
| 6 | 313 | 386 | 354 | 411 | 205 | 334 | 309 | 384 | 312 | 306 | 299 |
| 7 | 312 | 152 | 282 | 201 | 290 | 89 | 342 | 134 | 207 | 281 | 354 |
| 8 | 321 | 358 | 291 | 198 | 311 | 349 | 299 | 395 | 254 | 322 | 390 |
| 9 | 310 | 200 | 293 | 254 | 165 | 201 | 257 | 398 | 289 | 271 | 253 |
| 10 | 300 | 389 | 402 | 352 | 300 | 299 | 380 | 388 | 352 | 327 | 301 |

Common yogurt products were fed patients with low serum glucose level in an amount of 200 g a day plus normal diet for 3 weeks. The measurement of serum glucose level was performed every morning before meals. The results were listed in the following Table 7. The level was increased to 262 mg/dL (n=9) a week after the feeding, 315 mg/dL (n=7) two weeks after the feeding and 355 mg/dL (n=6) three weeks after the feeding. Accordingly, it was confirmed that there was no dropping effect of serum glucose level in yogurt diet group.

TABLE 7

The change of serum glucose level (mg/dL) in diabetics fed with yogurt diet

| Patients | \multicolumn{11}{c}{Days} |
|---|---|---|---|---|---|---|---|---|---|---|---|
|  | 1 | 3 | 5 | 7 | 9 | 11 | 13 | 15 | 17 | 19 | 21 |
| 1 | 115 | 124 | 109 | 139 | 160 | 228 | 219 | 301 | 340 | 346 | 352 |
| 2 | 180 | 175 | 198 | 242 | 270 | 292 | 354 | 347 | 395 | 404 | 412 |
| 3 | 200 | 254 | 380 |  |  |  |  |  |  |  |  |
| 4 | 138 | 135 | 124 | 178 | 141 | 185 | 152 | 173 | 195 | 192 | 189 |
| 5 | 225 | 240 | 290 | 370 | 423 |  |  |  |  |  |  |
| 6 | 192 | 209 | 284 | 319 | 325 | 398 | 425 | 387 |  |  |  |
| 7 | 240 | 290 | 317 | 325 | 354 | 349 | 402 | 372 | 386 | 392 | 398 |
| 8 | 128 | 119 | 145 | 130 | 135 | 217 | 249 | 299 | 284 | 317 | 350 |
| 9 | 219 | 260 | 292 | 343 | 392 | 417 | 449 |  |  |  |  |
| 10 | 208 | 218 | 240 | 315 | 342 | 379 | 315 | 328 | 427 | 429 | 430 |

Lactic acid fermented solution of mushroom obtained in Example 42 was fed 10 men with diabetes mellitus who exhibited the same level (321 mg/dL) of serum glucose level as control in amount of 200 g a day plus normal diet for 3 weeks. The measurement of serum glucose level was performed at seven before meals. The results were listed in the following Table 8. The level was decreased to 207 mg/dL (n=10) a week after the feeding, 166 mg/dL (n=7) two weeks after the feeding and 150 mg/dL (n=10) three weeks after the feeding. Also, the average serum glucose level in 8 of 10 patients with diabetes mellitus was dropped to 121 mg/dL (n=8), and in particular, to 123 mg/dL 5 days after the feeding.

Accordingly, the results showed that lactic acid fermented solution of mushroom according to the present invention had a significant effect for dropping serum glucose level.

TABLE 8

The change of serum glucose level (mg/dL) in diabetics
fed with lactic acid fermented solution of mushroom

| patients | \multicolumn{11}{c}{Days} |
|---|---|---|---|---|---|---|---|---|---|---|---|
|  | 1 | 3 | 5 | 7 | 9 | 11 | 13 | 15 | 17 | 19 | 21 |
| 1 | 342 | 302 | 224 | 295 | 328 | 245 | 201 | 175 | 158 | 142 | 125 |
| 2 | 295 | 314 | 287 | 254 | 220 | 186 | 195 | 143 | 115 | 113 | 110 |
| 3 | 405 | 398 | 309 | 253 | 410 | 357 | 231 | 324 | 243 | 447 | 310 |
| 4 | 292 | 275 | 251 | 269 | 224 | 220 | 228 | 219 | 124 | 141 | 158 |
| 5 | 215 | 187 | 250 | 149 | 148 | 177 | 136 | 200 | 145 | 134 | 122 |
| 6 | 400 | 322 | 254 | 159 | 217 | 208 | 178 | 125 | 167 | 158 | 149 |

TABLE 8-continued

The change of serum glucose level (mg/dL) in diabetics
fed with lactic acid fermented solution of mushroom

| patients | Days | | | | | | | | | | |
|---|---|---|---|---|---|---|---|---|---|---|---|
| | 1 | 3 | 5 | 7 | 9 | 11 | 13 | 15 | 17 | 19 | 21 |
| 7 | 338 | 275 | 199 | 228 | 145 | 155 | 101 | 75 | 98 | 99 | 99 |
| 8 | 216 | 158 | 131 | 69 | 147 | 111 | 92 | 108 | 125 | 114 | 103 |
| 9 | 295 | 289 | 123 | 118 | 101 | 92 | 97 | 95 | 99 | 100 | 101 |
| 10 | 411 | 408 | 375 | 275 | 303 | 123 | 298 | 199 | 182 | 244 | 219 |

Experimental Example 4

The Contents of Mushroom Extract Effective for Dropping Serum Glucose Level

To determine the appropriate amounts of mushroom extract, the experiments were carried out using lactic acid fermented solution of mushroom obtained in Examples 40–43 and Comparative Examples 1–2 over 3 persons per each group.

As shown in the following Table 9 and as depicted in FIGS. 6a–6e, dropping effect of serum glucose level were insignificant in the concentration ranging from 0.01% to 0.5%, but the serum glucose level was no longer increased in the concentration of not less than 0.1%. Furthermore, the pharmacological effect was most excellent at the level of 5%, but resulted in serious hypoglycemia at the level of not less than 10%. Accordingly, it can be concluded that the optimum amount of mushroom extract as added was about 200 g corresponding to the range of 0.1% to 7%. However, it can be varied with sex, age, body weight and severity of diabetes mellitus.

gistic effect of mushroom extract and lactic acid bacteria, a patient with diabetes mellitus was continuously fed with mushroom extract and lactic acid fermented solution of mushroom according to the present invention. The intake of lactic acid fermented solution of mushroom according to the present invention and mushroom extract was performed after the measurement of serum glucose level, but before breakfast and supper. The measurement of serum glucose level was performed at seven every two days.

First, lactic acid fermented solution of mushroom obtained in Example 42 was fed a patient for 36 days, and subsequently cut the feeding for 6 days. Thereafter, when the serum glucose level began to increase, the same amount of mushroom extract as lactic acid fermented solution of mushroom was fed the patient. The change of serum glucose level was monitored at intervals of predetermined time (2 days)

As shown in the following Table 10 and accompanying FIG. 7, the serum glucose level was sharply dropped for 10 days, and then stabilized at 100 (mg/dL) for about 20 days (see "A" in FIG. 7). However, since the feeding was cut, the

TABLE 9

The change of serum glucose level (mg/dL) over the contents
of lactic acid fermented solution of mushroom in diabetics.

| Contents/patieuts | | Days | | | | | | | | | | |
|---|---|---|---|---|---|---|---|---|---|---|---|---|
| | | 1 | 3 | 5 | 7 | 9 | 11 | 13 | 15 | 17 | 19 | 21 |
| 0.01% | 1 | 212 | 219 | 230 | 299 | 372 | 402 | | | | | |
| | 2 | 107 | 109 | 101 | 98 | 123 | 108 | 127 | 92 | 99 | 104 | 109 |
| | 3 | 240 | 279 | 288 | 342 | 319 | 380 | 372 | 399 | | | |
| 0.1% | 1 | 244 | 259 | 210 | 149 | 232 | 300 | 198 | 212 | 201 | 211 | 220 |
| | 2 | 295 | 242 | 302 | 318 | 242 | 115 | 89 | 198 | 242 | 271 | 299 |
| | 3 | 192 | 200 | 114 | 75 | 221 | 208 | 182 | 191 | 180 | 167 | 154 |
| 0.5% | 1 | 288 | 271 | 249 | 262 | 199 | 190 | 175 | 294 | 205 | 177 | 149 |
| | 2 | 314 | 324 | 295 | 270 | 222 | 142 | 157 | 140 | 131 | 126 | 120 |
| | 3 | 329 | 245 | 279 | 244 | 309 | 300 | 223 | 258 | 249 | 274 | 299 |
| 5% | 1 | 450 | 430 | 375 | 330 | 250 | 189 | 114 | 79 | 92 | 96 | 99 |
| | 2 | 387 | 301 | 254 | 199 | 125 | 100 | 69 | 72 | 89 | 86 | 82 |
| | 3 | 394 | 412 | 321 | 249 | 199 | 101 | 82 | 93 | 95 | 92 | 89 |
| 10% | 1 | 324 | 201 | 115 | 99 | 75 | 65 | | | | | |
| | 2 | 455 | 437 | 315 | 290 | 142 | 89 | 94 | 115 | 99 | 117 | 135 |
| | 3 | 400 | 399 | 387 | 300 | 224 | 202 | 103 | 140 | 109 | 90 | 70 |

The steady intake of lactic acid fermented solution of mushroom according to the present invention helped the serum glucose level be maintained to be normal in most of patients with type 2 diabetes mellitus.

Figure 7:
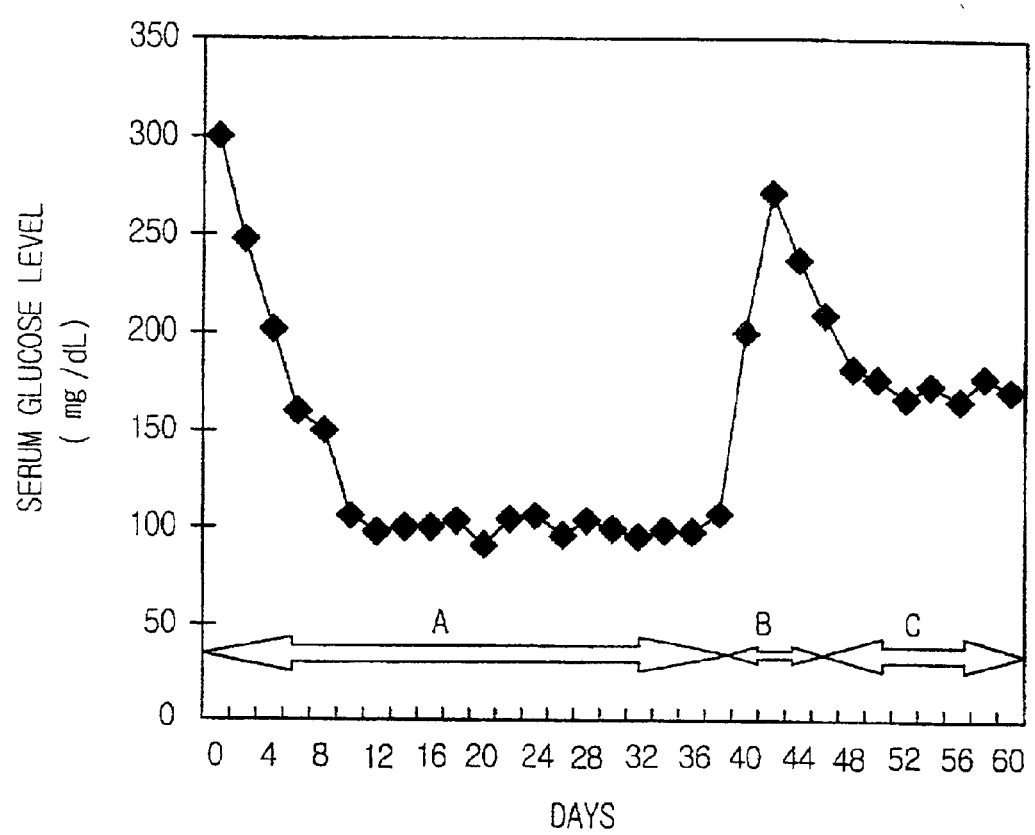
FIG. 7 is a graph showing the change of blood sugar level over the dietary history of lactic acid fermented solution of Ganderma lucidum obtained in Example 42 and the dietary history of Ganderma lucidum extract.

Experimental Example 5
Synergistic Effect of Mushroom Extract and Tactic Acid Bacteria To identify whether the drop of serum glucose level shown in Experimental Examples was occurred by a synerserum glucose level was increased to 276 (mg/dL) (see "B" in FIG. 7).

Subsequently, when the same amount of mushroom extract as lactic acid fermented solution of mushroom was fed the patient, the serum glucose level was slowly decreased. Thereafter, there was no significant change in serum glucose level (see "C" in FIG. 7).

TABLE 10

The change of serum glucose level (mg/dL) over the intake of lactic acid fermented solution of mushroom and mushroom extract in diabetics.

| Days | The change of serum glucose level over lactic acid fermented solution of mushroom | Days | The change of serum glucose level over diet cut | Days | The change of serum glucose over mushroom extract diet |
|---|---|---|---|---|---|
| 0 | 302 | 38 | 107 | 44 | 233 |
| 2 | 247 | 40 | 202 | 46 | 213 |
| 4 | 203 | 42 | 276 | 48 | 182 |
| 6 | 161 | | | 50 | 178 |
| 8 | 147 | | | 52 | 170 |
| 10 | 105 | | | 54 | 174 |
| 12 | 95 | | | 56 | 168 |
| 14 | 99 | | | 58 | 179 |
| 16 | 101 | | | 60 | 171 |
| 18 | 104 | | | | |
| 20 | 89 | | | | |
| 22 | 106 | | | | |
| 24 | 107 | | | | |
| 26 | 94 | | | | |
| 28 | 103 | | | | |
| 30 | 99 | | | | |
| 32 | 92 | | | | |
| 34 | 98 | | | | |
| 36 | 96 | | | | |

From the above results, it can be seen that there was a synergistic effect of mushroom extract and lactic acid bacteria on the drop of serum glucose level.

Lactic acid fermented solution of mushroom produced in accordance with the method according to the present invention is excellent in its taste, flavor and gustatoriness, and effective for inhibiting the formation of peroxidized lipid and the drop of serum glucose level. Accordingly, the present invention is applicable in pharmacology and food industry.

The present disclosure relates to subject matter contained in priority Korean Patent Application Nos. 2001-24513, filed on May 7, 2001, 2001-54236, filed on Sep. 4, 2001, and 2001-73033, filed on Nov. 22, 2001, the contents of all of which are herein expressly incorporated by reference in their entireties.

What is claimed is:

1. A method for preparing lactic acid fermented solution of mushroom comprising:
   (a) preparing a mushroom ingredients-containing medium by homogenizing a medium mixture comprising from 0.1–10% by weight of mushroom ingredients from fruit bodied or mycelia of mushroom, 1–50% by weight of defatted milk, 0.1–20% by weight of sugar and the balance of purified water, heat-treating the homogenized medium mixture at a temperature ranging 75–110° C. for 15–40 minutes, and cooling the heat-treated medium mixture to a temperature ranging 35–40° C.;
   (b) inoculating lactic acid strain bacteria onto the mushroom ingredients-containing medium;
   (c) culturing the strain-inoculated medium; and
   (d) aging the cultured medium.

2. The method according to claim 1, wherein the medium mixture (a) consists of 0.1–10% by weight of mushroom ingredients, 1–20% by weight of defatted milk, 0.1–20% by weight of sugar and the balance of purified water.

3. The method according to claim 1, wherein the strain (b) is inoculated in an amount of 1–10% by weight of cold storaged or heat-treated lactic acid bacteria, based on the total weight of said mushroom ingredients-containing medium.

4. The method according to claim 3, wherein the strain to be inoculated is *Lactobacillus bulgaricus*.

5. The method according to claim 3, wherein the strain is heat-treated lactic acid bacteria.

6. The method according to claim 5, wherein the heat-treatment is carried out by placing a cold-stored strain in an incubator and incubating the strain at a temperature from 25–40° C.

7. The method according to claim 1, wherein the culturing is carried out within the range of 35–40° C. for 3–20 hours.

8. The method according to claim 7, wherein the culturing is carried out for 3–6 hours.

9. The method according to claim 1, wherein the aging is carried out at a temperature from 3–5° C. for 10–20 hours.

10. The method according to claim 1, wherein the mushroom ingredients are obtained from at least one mushroom selected from the group consisting of *Agaricus blazei, Ganderma lucidum, Grifola frondosa, Elfbingia applanata, Pleurotus osteratus, Agaricus bisporus, Flammulina velutipes, Lentinus edodes* and *Crdyceps* spp.

11. A method for preparing lactic acid fermented solution of mushroom comprising:
   (a) preparing a mushroom ingredients-containing medium comprising the sub-steps of:
      (i) obtaining mushroom ingredients from fruit bodies of mycelia of at least one mushroom selected from the group consisting of *Agaricus blazei, Ganderma lucidum, Grifola frondosa, Elfbingia applanata, Pleurotus osteratus, Agaricus bisporus, Flammulina velutipes, Lentinus edodes* and *Crdyceps* spp, by grinding or extracting;
      (ii) preparing a medium mixture including the mushroom ingredients;
      (iii) heat-treating the prepared medium mixture at a temperature ranging 75–110° C. for 15–40 minutes; and
      (iv) cooling the heat-treated medium mixture to a temperature ranging 35–40° C.;
   (b) inoculating lactic acid strain bacteria onto the mushroom ingredients-containing medium;

(c) culturing the strain-inoculated medium; and
(d) aging the cultured medium.

12. The method according to claim 11, wherein the mushroom ingredients in (i) are obtained from *Ganderma lucidum* extract.

13. The method according to claim 11, wherein the medium mixture in (ii) consists of 0,1–10% by weight of mushroom ingredients, 1–50% by weight of defatted milk, 0.1–20% by weight of sugar and the balance of purified water.

14. A method for preparing lactic acid fermented solution of mushroom comprising:
(a) preparing a mushroom ingredients-containing medium comprising the sub-steps of
  (i) obtaining mushroom ingredients from fruit bodies of mycelia of *Lentinus edodes, Pleurotus osteratus* and *Ganderma lucidum*, by grinding or extracting;
  (ii) preparing a medium mixture including the mushroom ingredients;
  (iii) heat-treating the prepared medium mixture at a temperature ranging 75–110° C. for 15–40 minutes; and
  (iv) cooling the heat-treated medium mixture to a temperature ranging 35–40° C.;
(b) inoculating lactic acid strain bacteria onto the mushroom ingredients-containing medium;
(c) culturing the strain-inoculated medium; and
(d) aging the cultured medium.

15. The method according to claim 14, wherein the medium mixture in (ii) consists of 0.1–10% by weight of mushroom ingredients, 1–50% by weight of defatted milk, 0.1–20% by weight of sugar and the balance of purified water.

16. A lactic acid fermented solution of mushroom comprising effective ingredients for dropping blood sugar level produced by fermenting a mushroom ingredients-containing medium with lactic acid bacteria, in which the mushroom ingredients are obtained from *Ganderma lucidum* extract.

17. A lactic acid fermented solution of mushroom comprising effective ingredients for dropping the formation of peroxidized lipid in serum produced by fermenting a mushroom ingredients-containing medium with lactic acid bacteria, in which the mushroom ingredients are obtained from a mixture of *Lentinus edodes, Pleurotus osteratus* and *Ganderma lucidum*.

* * * * *

UNITED STATES PATENT AND TRADEMARK OFFICE
CERTIFICATE OF CORRECTION

PATENT NO. : 6,841,180 B2
DATED : January 11, 2005
INVENTOR(S) : B.K. Kim et al.

It is certified that error appears in the above-identified patent and that said Letters Patent is hereby corrected as shown below:

<u>Title page,</u>
Item [57], ABSTRACT,
Line 5, "mushrooms" should be -- mushroom --.

Signed and Sealed this

Twenty-third Day of August, 2005

JON W. DUDAS
*Director of the United States Patent and Trademark Office*